US012286678B2

(12) United States Patent
Espiritu et al.

(10) Patent No.: US 12,286,678 B2
(45) Date of Patent: Apr. 29, 2025

(54) CANCER RISK BASED ON TUMOUR CLONALITY

(71) Applicants: ONTARIO INSTITUTE FOR CANCER RESEARCH (OICR), Toronto (CA); UNIVERSITY HEALTH NETWORK, Toronto (CA)

(72) Inventors: Shadrielle Melijah G. Espiritu, Kitchener (CA); Yiyang Liu, Woodbridge (CA); Paul C. Boutros, Toronto (CA); Robert G. Bristow, Toronto (CA)

(73) Assignees: Ontario Institute for Cancer Research (OICR), Toronto (CA); University Health Network, Toronto (CA)

(*) Notice: Subject to any disclaimer, the term of this patent is extended or adjusted under 35 U.S.C. 154(b) by 963 days.

(21) Appl. No.: 16/496,196

(22) PCT Filed: Mar. 20, 2018

(86) PCT No.: PCT/CA2018/000058
§ 371 (c)(1),
(2) Date: Sep. 20, 2019

(87) PCT Pub. No.: WO2018/170578
PCT Pub. Date: Sep. 27, 2018

(65) Prior Publication Data
US 2020/0032349 A1 Jan. 30, 2020

Related U.S. Application Data

(60) Provisional application No. 62/473,875, filed on Mar. 20, 2017.

(51) Int. Cl.
| | | |
|---|---|---|
| *C12Q 1/6886* | (2018.01) | |
| *G16B 10/00* | (2019.01) | |
| *G16B 20/20* | (2019.01) | |
| *G16B 30/10* | (2019.01) | |
| *G16B 40/10* | (2019.01) | |
| *G16B 45/00* | (2019.01) | |
| *G16H 50/20* | (2018.01) | |
| *G16H 50/30* | (2018.01) | |
| *G16H 50/50* | (2018.01) | |

(52) U.S. Cl.
CPC .......... *C12Q 1/6886* (2013.01); *G16B 10/00* (2019.02); *G16B 20/20* (2019.02); *G16B 30/10* (2019.02); *G16B 40/10* (2019.02); *G16B 45/00* (2019.02); *G16H 50/20* (2018.01); *G16H 50/30* (2018.01); *G16H 50/50* (2018.01); *C12Q 2600/156* (2013.01)

(58) Field of Classification Search
CPC ...... C12Q 1/6886; G16H 50/50; G16H 50/30; G16H 50/20; G16B 30/10; G16B 20/20; G16B 10/00; G16B 45/00
See application file for complete search history.

(56) References Cited

FOREIGN PATENT DOCUMENTS

WO   WO 2017185165   11/2017

OTHER PUBLICATIONS

Yates et al. "Subclonal Diversificaiton of Primary Breast Cancer Revealed by Multiregion Sequencing" Nature Medicine (2015) vol. 21, No. 7, pp. 751-759 (Year: 2015).*
Alexandrov et al., "Signatures of mutational processes in human cancer." *Nature* 2013, 500, 415-421.
Bergmann et al., "Conpair: concordance and contamination estimator for matched tumor-normal pairs." *Bioinformatics* 2016, 32(20), 3196-3198.
Bhagwat, "Searching NCBI's dbSNP database." *Current Protocols in Bioinformatics* 2010, 1, 1-19.
Boutros et al., "Spatial genomic heterogeneity within localized, multifocal prostate cancer" *Nature Genetics* 2015, 47 (7), 736-745.
Chiang et al., "SpeedSeq: ultra-fast personal genome analysis and interpretation." *Nature Methods* 2015, 12, 966-968.
Cibulskis et al., "ContEst: estimating cross-contamination of human samples in next-generation sequencing data." *Bioinformatics* 2011, 27(18), 2601-2602.
Cibulskis et al., "Sensitive detection of somatic point mutations in impure and heterogeneous cancer samples." *Nature Biotechnology* 2013, 31(3), 213-219.
Cooper et al., "Analysis of the genetic phylogeny of multifocal prostate cancer identifies multiple independent clonal expansions in neoplastic and morphologically normal prostate tissue" *Nature Genetics* 2015, 47(4), 367-372.
Cuzick et al., "Prognostic value of an RNA expression signature derived from cell cycle proliferation genes in patients with prostate cancer: a retrospective study." *The Lancet. Oncology* 2011, 12, 245-255.
Dalma-Weiszhausz et al., "The affymetrix GeneChip® platform: An overview." *Methods in Enzymology* 2006, 410, 3-28.
De Bruin et al., "Spatial and temporal diversity in genomic instability processes defines lung cancer evolution." *Science* 2014, 346, 251-256.
Demichelis et al., "Distinct genomic aberrations associated with ERG rearranged prostate cancer." *Genes, chromosomes & cancer* 2009, 48, 366-380.

(Continued)

*Primary Examiner* — Jerry Lin
(74) *Attorney, Agent, or Firm* — Norton Rose Fulbright US LLP

(57) ABSTRACT

In an aspect, there is provided a method for diagnosing or prognosing a subject with cancer, the method comprising: providing cancer DNA sequencing data from a cancer sample comprising cancer DNA from the subject; comparing the cancer DNA sequencing data with control DNA sequencing data to determine genetic aberrations; determining, from the genetic aberrations, the clonal and subclonal populations present in the sample; constructing a phylogenetic map of the clonal and subclonal populations; assigning to the subject a risk level associated with a better or worse patient outcome or response to therapy; wherein a relatively higher risk level is associated with a higher level of evolution and number of subclonal populations and a relatively lower risk level is associated with a lower level of evolution and number of subclonal populations.

13 Claims, 29 Drawing Sheets

(56) References Cited

OTHER PUBLICATIONS

Deshwar et al., "PhyloWGS: Reconstructing subclonal composition and evolution from whole-genome sequencing of tumors." *Genome Biol.* 2015, 16, 35.
Ding et al., "Feature-based classifiers for somatic mutation detection in tumour-normal paired sequencing data." *Bioinformatics* 2012, 28, 167-175.
Erho et al., "Discovery and validation of a prostate cancer genomic classifier that predicts early metastasis following radical prostatectomy." *PLoS One* 2013, 8, e66855.
Fraser et al., "Genomic hallmarks of localized non-indolent prostate cancer" *Nature* 2017, 541(7637), 359-364.
Genome Reference Consortium. , <URL: https://www.ncbi.nlm.nih.gov/grc/human> accessed on Nov. 25, 2019.
George et al. "Survival analysis and regression models." *Journal of Nuclear Cardiology* 2014, 21(4), 686-694.
Gerlinger et al., "Intratumor heterogeneity and branched evolution revealed by multiregion sequencing" *N Engl J Med* 2012, 366, 883-892.
Gundem et al., "The evolutionary history of lethal metastatic prostate cancer." *Nature* 2015, 520, 353-357.
Ha et al., "TITAN: inference of copy No. architectures in clonal cell populations from tumor whole-genome sequence data." *Genome Res.* 2014, 24, 1881-1893.
Hieronymus et al., "Copy number alteration burden predicts prostate cancer relapse." *Proceedings of the National Academy of Sciences of the United States of America* 2014, 111, 11139-11144.
Hong et al., "Tracking the origins and drivers of subclonal metastatic 5 expansion in prostate cancer." *Nature communications* 2015, 6(6605), 1-10.
International Search Report and Written Opinion issued in counterpart Application No. PCT/CA2018/000058, dated Jun. 21, 2018.
Jiao et al., "Inferring clonal evolution of tumors from single nucleotide somatic mutations." *BMC Bioinformatics* 2014, 15(35), 16 pages.
Klein et al., "A 17-gene assay to predict prostate cancer aggressiveness in the context of Gleason grade heterogeneity, tumor multifocality, and biopsy undersampling." *Eur Urol.* 2014, 66, 550-560.
Koboldt et al., "Using VarScan 2 for germline variant calling and somatic mutation detection." *Current Protocols in Bioinformatics* 2013, 44, 15.4.1-15.4.17.
Lalonde et al., "Translating a Prognostic DNA Genomic Classifier into the Clinic: Retrospective Validation in 563 Localized Prostate Tumors." *European Urology* 2017, 72(1), 22-31.
Lalonde et al., "Tumour genomic and microenvironmental heterogeneity for integrated prediction of 5-year biochemical recurrence of prostate cancer: a retrospective cohort study." *Lancet Oncol* 2014, 15, 1521-1532.
Langmead et al., "Ultrafast and memory-efficient alignment of short DNA sequences to the human genome." *Genome Biology* 2008, 10, R25-5.
Larson et al., "SomaticSniper: identification of somatic point mutations in whole genome sequencing data." *Bioinformatics* 2012, 28, 311-317.
Li et al., "Fast and accurate short read alignment with Burrows-Wheeler transform." *Bioinformatics* 2009, 25(14), 1754-1760.
Li et al., "The sequence alignment/map format and SAMtools." *Bioinformatics* 2009, 25, 2078-2079.
Lllumina, "A high-resolution view of the entire genome." <URL:https://www.illumina.com/techniques/sequencing/dna-sequencing/whole-genome-sequencing.html> accessed Nov. 25, 2019.
Mardis, "Next-generation DNA sequencing methods." *Annual Review of Genomics and Human Genetics* 2008, 9, 387-402.
McKenna et al. "The Genome Analysis Toolkit: a MapReduce framework for analyzing next-generation DNA sequencing data." *Genome Research* 2010, 20, 1297-1303.
McPherson et al., "Divergent modes of clonal spread and intraperitoneal mixing in high-grade serous ovarian cancer." *Nature genetics* 2016, 48, 758-767.
Miller et al., "SciClone: inferring clonal architecture and tracking the spatial and temporal patterns of tumor evolution." *PLoS Computational Biology* 2014,10(8), 15 pages.
Nik-Zainal et al., "The life history of 21 breast cancers" *Cell* 2012, 149, 994-1007.
Notta et al. "A renewed model of pancreatic cancer evolution based on genomic rearrangement patterns." *Nature* 2016, 538, 378-382.
Novocraft. 2010. < URL: http://www.novocraft.com/ > accessed on Nov. 25, 2019.
Oesper et al., "THetA: inferring intra-tumor heterogeneity from high-throughput DNA sequencing data." *Genome Biology* 2013, 14(R80), 21 pages.
Pinto et al., "Functional impact of global rare copy number variation in autism spectrum disorders" *Nature* 2010, 466, 368-372.
Pritchard et al., "Inherited DNA-Repair Gene Mutations in Men with Metastatic Prostate Cancer." *The New England journal of medicine* 2016, 375, 443-453.
Radenbaugh et al., "Radia: RNA and DNA integrated analysis for somatic mutation detection." *PLoS One* 2014, 9(11), 11 pages.
Reimand et al., "g:Profiler-a web server for functional interpretation of gene lists (2016 update)." *Nucleic acids research* 2016, 44, 7 pages.
Ross-Adams et al., "Integration of copy No. and transcriptomics provides risk stratification in prostate cancer: A discovery and validation cohort study." *EBioMedicine* 2015, 2, 1133-1144.
Roth et al., "PyClone: statistical inference of clonal population structure in cancer." *Nature Methods* 2014, 11(4), 396-398.
Sanger et al. "DNA sequencing with chain-terminating inhibitors." *Proceedings of the National Academy of Sciences. U.S.A.* 1977, 74, 5463-5467.
Saunders et al., "Strelka: accurate somatic small-variant calling from sequenced tumor-normal sample pairs." *Bioinformatics* 2012, 28(14), 1811-1817.
Senbabaoglu et al., "Critical limitations of consensus clustering in class discovery." *Sci Rep* 2014, 4(6207) 13 pages.
Soares et al. "Next-generation sequencing of miRNAs with Roche 454 GS-FLX technology: steps for a successful application." *Methods in Molecular Biology* 2012, 822, 189-204.
Stephens et al., "Massive genomic rearrangement acquired in a single catastrophic event during cancer development." *Cell* 2011, 144, 27-40.
Taylor et al., "Germline BRCA2 mutations drive prostate cancers with distinct evolutionary trajectories" *Nature Communications* 2017, 8(13671), 1-10.
Taylor et al., "Integrative genomic profiling of human prostate cancer." *Cancer Cell* 2010, 18, 11-22.
The 1000 Genomes Project Consortium. "A global reference for human genetic variation." *Nature* 2015, 526, 68-74.
The Cancer Genome Atlas Research Network, "The Molecular Taxonomy of Primary Prostate Cancer" *Cell* 2015, 163, 1011-1025.
ThermoFisher Scientific. "Ion Torrent next-generation sequencing technology." <URL: https://www.thermofisher.com/ca/en/home/life-science/sequencing/next-generation-sequencing/ion-torrent-next-generation-sequencing-technology.html > accessed on Nov. 25, 2019.
Vogelstein et al., "Genetic alterations during colorectal-tumor development." *The New England journal of medicine* 1988, 319, 525-532.
Wang et al., "ANNOVAR: functional annotation of genetic variants from high-throughput sequencing data." *Nucleic Acids Res.* 2010, 38(16), 7 pages.
Wilkerson et al., "ConsensusClusterPlus: a class discovery tool with confidence assessments and item tracking." *Bioinformatics* 2010, 26, 1572-1573.
Xi et al., "BIC-seq: a fast algorithm for detection of copy number alterations based on high-throughput sequencing data." *Genome Biology* 2010, 11 (S1):010.

\* cited by examiner

CANCER RISK BASED ON TUMOUR CLONALITY

This application is a national phase application under 35 U.S.C. § 371 of International Application No. PCT/CA2018/000058, filed Mar. 20, 2018, which claims priority of U.S. Provisional Patent Application No. 62/473,875 filed Mar. 20, 2017.

FIELD OF THE INVENTION

The invention relates to cancer diagnosis and prognosis.

BACKGROUND OF THE INVENTION

Tumourigenesis proceeds through a sequential series of mutational events, some incremental and others catastrophic (Notta et al. Nature in press). Some of these events confer a selective advantage on cancer cells, allowing cells to outcompete their neighbours, for example by overcoming selective pressures like hypoxia or telomere crisis. Spatio-genomic studies that sequenced multiple regions of a single tumour have suggested that this process leads to most solid tumours being comprised of multiple clones[3-5]. Clones can harbour both mutations common to all cells present in the tumour, called clonal mutations, and mutations specific to one evolutionary branch of the tumour, termed subclonal mutations. However because only small numbers of samples have received spatio-genomic study to date, the molecular origins and clinical consequences of tumour subclonality remain unclear.

SUMMARY OF THE INVENTION

In an aspect, there is provided a method for diagnosing or prognosing a subject with cancer, the method comprising: providing cancer DNA sequencing data from a cancer sample comprising cancer DNA from the subject; comparing the cancer DNA sequencing data with control DNA sequencing data to determine genetic aberrations; determining, from the genetic aberrations, the clonal and subclonal populations present in the sample; constructing a phylogenetic map of the clonal and subclonal populations; assigning to the subject a risk level associated with a better or worse patient outcome or response to therapy; wherein a relatively higher risk level is associated with a higher level of evolution and number of subclonal populations and a relatively lower risk level is associated with a lower level of evolution and number of subclonal populations.

In an aspect, there is provided a computer-implemented method of diagnosing or prognosing a subject with cancer comprising, the method comprising: receiving, at at least one processor, data reflecting cancer DNA sequencing data from a cancer sample comprising cancer cells from the subject; comparing, at the at least one processor, the cancer DNA sequencing data with control DNA sequencing data to determine genetic aberrations; determining, at the at least one processor, from the genetic aberrations, the subclonal populations present in the sample; constructing, at the at least one processor, a phylogenetic map of the subclonal populations; assigning, at the at least one processor, to the subject a risk level associated with a better or worse patient outcome; wherein a relatively higher risk level is associated with a higher level of evolution and number of subclonal populations, and a relatively lower risk level is associated with a lower level of evolution and number of subclonal populations.

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer readable medium having stored thereon a data structure for storing the computer program product described herein.

In an aspect, there is provided a device for diagnosing or prognosing a subject with cancer, the device comprising: at least one processor; and electronic memory in communication with the at one processor, the electronic memory storing processor-executable code that, when executed at the at least one processor, causes the at least one processor to: receive data reflecting cancer DNA sequencing data from a cancer sample comprising cancer cells from the subject; compare, at the at least one processor, the cancer DNA sequencing data with control DNA sequencing data to determine genetic aberrations; determine, at the at least one processor, from the genetic aberrations, the subclonal populations present in the sample; construct, at the at least one processor, a phylogenetic map of the subclonal populations; assign, at the at least one processor, to the subject a risk level associated with a better or worse patient outcome; wherein a relatively higher risk level is associated with a higher level of evolution and number of subclonal populations and a relatively lower risk level is associated with a lower level of evolution and number of subclonal populations.

BRIEF DESCRIPTION OF FIGURES

These and other features of the preferred embodiments of the invention will become more apparent in the following detailed description in which reference is made to the appended drawings wherein.

DETAILED DESCRIPTION

Figure 1:
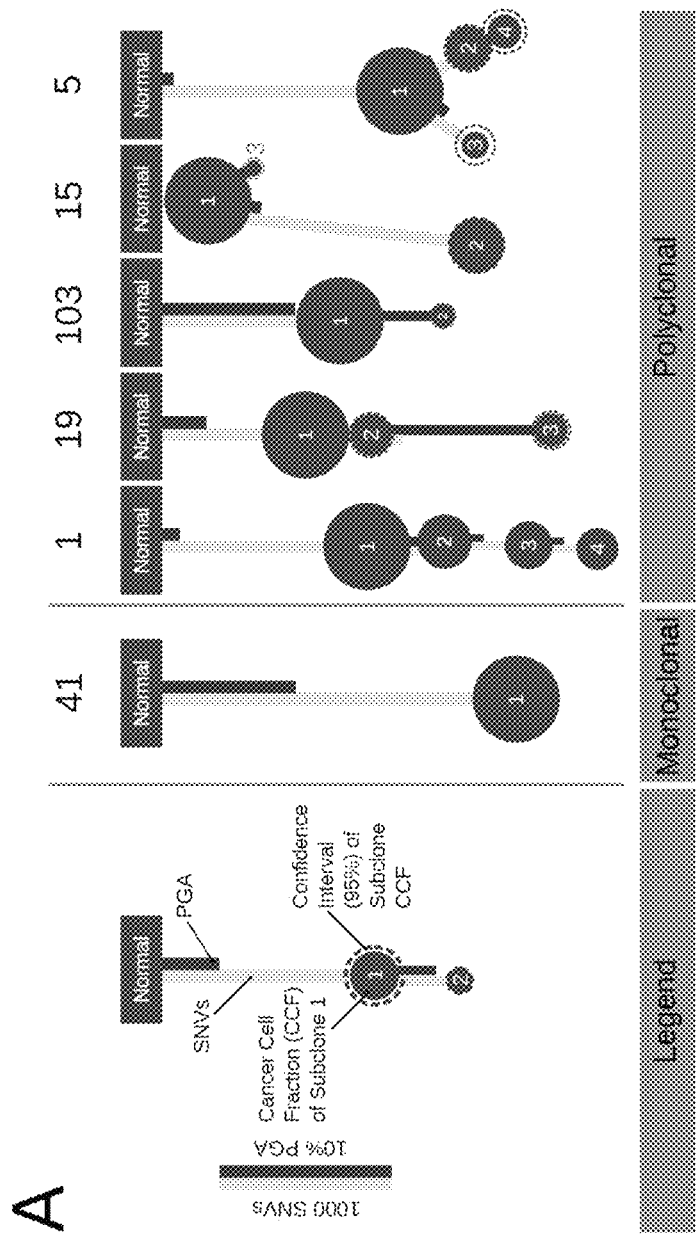
FIG. 1 shows Subclonal Architecture of Prostate Cancer. The diversity and frequency in architecture of prostate cancer evolution is summarized in (A). The tumours are divided into two clonality groups: monoclonal tumours only exhibit one clonal population in its evolution (41/184) and polyclonal tumours have at least one subclonal population (143/184). Mutational density is represented by the number of SNVs (yellow) and copy number aberrations (CNAs as assessed by PGA, blue) as the edge lengths. Cancer cell fraction for each subclone is represented by the node diameter, and the dashed circles show on standard deviation of the median cellularity across all tumours with identical trees. Representative trees are shown, selected as outlined in the Methods. Additional information on each individual tree was generated but not shown.

In the following description, numerous specific details are set forth to provide a thorough understanding of the invention. However, it is understood that the invention may be practiced without these specific details.

In order to investigate the molecular origins and clinical consequences of tumour subclonality, we chose to evaluate the subclonal architecture of primary prostate adenocarcinomas. Prostate cancer remains the most common non-skin malignancy in men. It is characterized by a long life-history, which leads to extensive intra-tumoural heterogeneity and subclones with wide genetic divergence at initial diagnosis. Prostate cancer is curable when localized, and the mutational landscape of early prostate cancer is well-characterized (Fraser et al. Nature in press and [8]). There is some preliminary evidence, from small number of multi-region sequencing studies, that tumours which have escaped the gland show clonal adaptatione[2]. However, it remains unclear how tumours evolve prior to initial diagnosis and therapy. For example, while tumours initiated in the presence of germline BRCA2 mutations harbour a unique mutational profile (Taylor et al. Nature Communications in press), it is unclear if other germline alleles influence tumour development[10]. It is natural to hypothesize that more genetically-diverse tumours will have worse outcome, but the clinical consequences of subclonal architecture and their impact on prognostic biomarkers remains unclear.

To address these issues, we reconstructed the subclonal architectures of 200 intermediate-risk prostate tumours using either a single surgical or biopsy specimen. We identify multiple cancer cell populations in 80% of cases.

Prostate cancer is a common, slow-growing tumour with a long natural life history characterized by a small number of driver mutations. To understand the evolutionary paths that lead to aggressive disease, we reconstructed the phylogenetic origins of 200 localized prostate tumours. 80% show evidence of multiple subclones, and subclonal architecture is associated with clinical measurements like Gleason grade and ETS gene fusion status. Most prostate cancer driver mutations are clonal, but a subset preferentially occur subclonally, and subclonal copy number subtypes are common. Mutational stresses change temporally over the course of disease progression, as shown by frequent switches in the pattern of trinucleotide signatures. Early tumour development is characterized by single nucleotide mutations, while later branching shows changes in trinucleotide mutational signatures and accumulation of copy number aberrations. Specific mutations are selectively biased to occur prior or following branched evolution, including MTOR and NKX3-1 and RB1. Patients with monoclonal tumours showed strikingly improved outcomes relative to those with polytumours, and the presence of polytumours confounds the accuracy of molecular prognostic assays. These data demonstrate that clinically-useful subclonal information can be derived from diagnostic biopsies, and provide a profile of prostate cancer evolution prior to its initial treatment and diagnosis.

Understanding disease clonality has clear clinical benefits: patients with multi-clonal tumours have distinctly worse outcome than those without, and existing prognostic biomarkers are confounded by subclonal copy-number changes Based on these findings, we also describe methods and devices for the diagnosis and/or prognosis of cancer based on clonality determinations.

In an aspect, there is provided a method for diagnosing or prognosing a subject with cancer, the method comprising: providing cancer DNA sequencing data from a cancer sample comprising cancer DNA from the subject; comparing the cancer DNA sequencing data with control DNA sequencing data to determine genetic aberrations; determining, from the genetic aberrations, the clonal and subclonal populations present in the sample; constructing a phylogenetic map of the clonal and subclonal populations; assigning to the subject a risk level associated with a better or worse patient outcome or response to therapy; wherein a relatively higher risk level is associated with a higher level of evolution and number of subclonal populations and a relatively lower risk level is associated with a lower level of evolution and number of subclonal populations.

The term "subject" as used herein refers to any member of the animal kingdom, preferably a human being and most preferably a human being that has, has had, or is suspected of having prostate cancer.

The term "sample" as used herein refers to any fluid (e.g. blood, urine, semen), cell, tumor or tissue sample from a subject which can be assayed for the biomarkers described herein.

The term "genetic material" used herein refers to materials found/originate in the nucleus, mitochondria and cytoplasm, which play a fundamental role in determining the structure and nature of cell substances, and capable of self-propagating and variation. In the context of the present methods, the genetic material is any material from which one can measure the biomarkers described herein. The genetic material is preferably DNA.

A "genetic aberration" is any change in genetic material that is unusual or uncommon when compared to wild-type or control genetic material. Genetic aberrations include deletions, substitutions, insertions, SNVs, translocations, hyper or hypo-methylation, copy number abberations and any other genetic mutations.

The term "prognosis" as used herein refers to the prediction of a clinical outcome associated with a disease subtype which is reflected by a reference profile such as a biomarker reference profile. The prognosis provides an indication of disease progression and includes an indication of likelihood of death due to cancer. The prognosis may be a prediction of metastasis, or alternatively disease recurrence. In one embodiment the clinical outcome class includes a better survival group and a worse survival group. The term "prognosing or classifying" as used herein means predicting or identifying the clinical outcome of a subject according to the subject's similarity to a reference profile or biomarker associated with the prognosis. For example, prognosing or classifying comprises a method or process of determining whether an individual has a better or worse survival outcome, or grouping individuals into a better survival group or a worse survival group, or predicting whether or not an individual will respond to therapy.

As used herein, the term "control" refers to a specific value or dataset that can be used to prognose or classify the value e.g the measured biomarker or reference biomarker profile obtained from the test sample associated with an outcome. In one embodiment, a dataset may be obtained from samples from a group of subjects known to have cancer having different tumor states and/or healthy individuals. The state or expression data of the biomarkers in the dataset can be used to create a control value that is used in testing samples from new patients. In some embodiments, a cohort of subjects is used to obtain a control dataset. A control cohort patients may be a group of individuals with or without cancer. Control sequencing data may include, a reference DNA sequence or reference DNA sequencing data. The reference DNA sequence(s) or sequencing data is in one embodiment, from an individual related to the subject. In another embodiment, the the reference DNA sequencing data from the subject.

As used herein, "overall survival" refers to the percentage of or length of time that people in a study or treatment group are still alive following from either the date of diagnosis or the start of treatment for a disease, such as cancer. In a clinical trial, measuring the overall survival is one way to see how well a new treatment works.

As used herein, "relapse-free survival" refers to, in the case of cancer, the percentage of or length of time that people in a study or treatment group survive without any signs or symptoms of that cancer after primary treatment for that cancer. In a clinical trial, measuring the relapse-free survival is one way to see how well a new treatment works. It is defined as any disease recurrence or relapse (local, regional, or distant).

The term "good survival" or "better survival" as used herein refers to an increased chance of survival as compared to patients in the "poor survival" group. For example, the biomarkers of the application can prognose or classify patients into a "good survival group". These patients are at a lower risk of death after surgery and can also be categorized into a "low-risk group".

The term "poor survival" or "worse survival" as used herein refers to an increased risk of disease progression or death as compared to patients in the "good survival" group. For example, biomarkers or genes of the application can prognose or classify patients into a "poor survival group". These patients are at greater risk of death or adverse reaction from disease or surgery, treatment for the disease or other causes, and can also be categorized into a "high-risk group".

A person skilled in the art would understand how to implement differing cut-offs for good survival vs. worse survival, depending on the clinical outcome one is predicting and the biomarkers being assayed.

As used herein, a "phylogenetic map" or "phylogeny" as it relates to subclonal populations is an organization or clustering of various subclonal populations by the evolutionary development, mutation and/or diversification of cells within a subject, for example, cancer cells within a tumour. In an embodiment, the phylogenetic maps are phylogenetic trees, which can be classified in different ways, such as by shape (linear vs. branching), number of subpopulations (e.g. monoclonal for a single population, polyclonal for >1), or number of ancestral tumours (e.g. polytumours). Computational approaches that can assist in creating phylogenies include, but are not limited to, PhyloWGS[29], PhyloSub[30], PyClone[31], SciClone[32], and ThetA[33].

As used herein "next generation sequencing" or "high-throughput sequencing" refers to technologies that allow sequencing of DNA and RNA much more quickly and cheaply than the previously used Sanger sequencing. This platform opens new ways and protocols in determining gene expression and identifying fundamental biological knowledge[1]. Sequencing can be performed at a whole-genome level, exome-level, de novo, or targeted at specific locations. A few such sequencing technologies include, but are not limited to, Illumina Solexa sequencing[2], Roche 454 sequencing[3], Ion torrent and SOLiD sequencing[4]. These methods provide superior advantages over the previous Sanger sequencing technology[5] in terms of cost, speed, accuracy, and sample size.

In some embodiments, the control DNA sequencing data is DNA sequencing data from a sample comprising normal cells from the subject;

In some embodiments, the cancer sample comprises cancer cells, and is preferably a tumour sample, further preferably a tumour sample from a primary site.

In some embodiments, the DNA sequencing data is generated using high-throughput sequencing.

In some embodiments, the method further comprises after step (a), sequence alignment of the DNA sequencing data against a common reference assembly to generate binary alignment/maps (BAMs) or sequence alignment maps (SAMs). IN addition, the method preferably further comprises performing a sequence alignment quality check.

In some embodiments, the sequence alignment quality check comprises at least one of: ensuring expected read coverage of each BAM; ensuring properly formatted BAM headers; removing duplicative reads by soft- or hard-filtering, improving alignment quality by local realignment; and performing validity downstream analysis on a small subset of the BAMs.

In some embodiments, the genetic aberrations comprise at least one of single nucleotide variants and copy number aberrations.

In some embodiments, the method further comprises performing a callset quality check. Preferably, the callset quality check comprises at least one of: applying an recurrence, intersection or union of calls; filtering out non-confidence calls against known whitelists and blacklists; and maintaining specific length of copy number aberrations.

In some embodiments, determining the subclonal populations present in the cancer sample comprises determining at least one of the variant allele frequencies and cellular prevalence.

In some embodiments, constructing the phylogenetic map of the subclonal populations comprises clustering the subclonal populations based on variant allele frequencies and cellular prevalence.

Cancers that are assessable by the invention may include adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, wilms tumor. In some embodiments, the cancer is prostate cancer.

Figure 6:
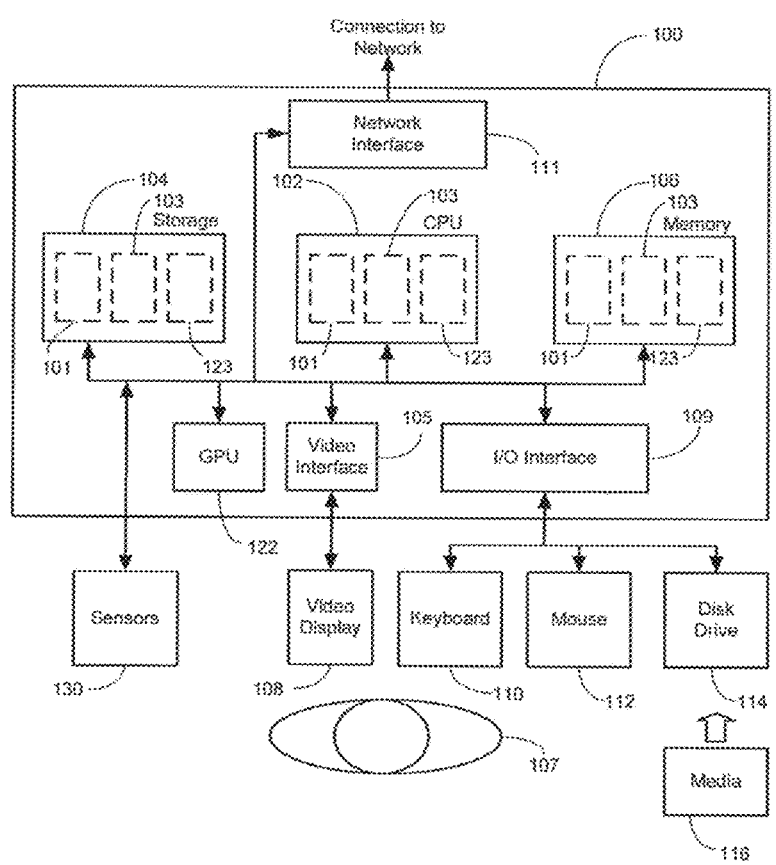
FIG. 6 shows a suitable configured computer device, and associated communications networks, devices, software and firmware to provide a platform for enabling one or more embodiments as described herein.

The present system and method may be practiced in various embodiments. A suitably configured computer device, and associated communications networks, devices, software and firmware may provide a platform for enabling one or more embodiments as described above. By way of example, FIG. 6 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 115, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 100 to communicate with other suitably configured data processing systems (not shown). One or more different types of sensors 135 may be used to receive input from various sources.

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present invention. In case of more than computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

In an aspect, there is provided a computer-implemented method of diagnosing or prognosing a subject with cancer comprising, the method comprising: receiving, at at least one processor, data reflecting cancer DNA sequencing data from a cancer sample comprising cancer cells from the subject; comparing, at the at least one processor, the cancer DNA sequencing data with control DNA sequencing data to determine genetic aberrations; determining, at the at least one processor, from the genetic aberrations, the subclonal populations present in the sample; constructing, at the at least one processor, a phylogenetic map of the subclonal populations; assigning, at the at least one processor, to the subject a risk level associated with a better or worse patient outcome; wherein a relatively higher risk level is associated with a higher level of evolution and number of subclonal populations, and a relatively lower risk level is associated with a lower level of evolution and number of subclonal populations.

In an aspect, there is provided a computer program product for use in conjunction with a general-purpose computer having a processor and a memory connected to the processor, the computer program product comprising a computer readable storage medium having a computer mechanism encoded thereon, wherein the computer program mechanism may be loaded into the memory of the computer and cause the computer to carry out the method described herein.

In an aspect, there is provided a computer readable medium having stored thereon a data structure for storing the computer program product described herein.

In an aspect, there is provided a device for diagnosing or prognosing a subject with cancer, the device comprising: at least one processor; and electronic memory in communication with the at one processor, the electronic memory storing processor-executable code that, when executed at the at least one processor, causes the at least one processor to: receive data reflecting cancer DNA sequencing data from a cancer sample comprising cancer cells from the subject; compare, at the at least one processor, the cancer DNA sequencing data with control DNA sequencing data to determine genetic aberrations; determine, at the at least one processor, from the genetic aberrations, the subclonal populations present in the sample; construct, at the at least one processor, a phylogenetic map of the subclonal populations; assign, at the at least one processor, to the subject a risk level associated with a better or worse patient outcome; wherein a relatively higher risk level is associated with a higher level of evolution and number of subclonal populations and a relatively lower risk level is associated with a lower level of evolution and number of subclonal populations.

As used herein, "processor" may be any type of processor, such as, for example, any type of general-purpose microprocessor or microcontroller (e.g., an Intel™ x86, PowerPC™, ARM™ processor, or the like), a digital signal processing (DSP) processor, an integrated circuit, a field programmable gate array (FPGA), or any combination thereof.

As used herein "memory" may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), or the like. Portions of memory 102 may be organized using a conventional file system, controlled and administered by an operating system governing overall operation of a device.

As used herein, "computer readable storage medium" (also referred to as a machine-readable medium, a processor-readable medium, or a computer usable medium having a computer-readable program code embodied therein) is a medium capable of storing data in a format readable by a computer or machine. The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The computer readable storage medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the computer readable storage medium. The instructions stored on the computer readable storage medium can be executed by a processor or other suitable processing device, and can interface with circuitry to perform the described tasks.

As used herein, "data structure" a particular way of organizing data in a computer so that it can be used efficiently. Data structures can implement one or more particular abstract data types (ADT), which specify the operations that can be performed on a data structure and the computational complexity of those operations. In comparison, a data structure is a concrete implementation of the specification provided by an ADT.

The advantages of the present invention are further illustrated by the following examples. The examples and their particular details set forth herein are presented for illustration only and should not be construed as a limitation on the claims of the present invention.

EXAMPLE 1

Methods and Materials
Patient Cohort

We analyzed a cohort of 200 localized prostate tumours with published whole-genome sequences of both tumour samples drawn from the index lesion of the tumour and matched blood-based normal reference samples (Fraser et al. Nature in press). Briefly, all patients were diagnosed with localized prostate cancer and had clinical Gleason Scores of 3+3, 3+4 or 4+3. They were treated with either image-guided radiotherapy (in which case a pre-treatment frozen biopsy was analyzed) or surgery (in which case a fresh-frozen post-operative specimen was analyzed). Samples were obtained from the University Health Network and the Centre Hospitalier Universitaire de Quebec. Whole blood was collected as a normal reference. Informed consent was obtained at the time of clinical follow-up from all patients, and ethics approval was obtained through the University Health Network Research Ethics Board under study numbers UHN 06-0822-CE, UHN 11-0024-CE and CHUQ 2012-913:H12-03-192. All specimens were reviewed for Gleason grade and cellularity. Up to 200 ng of DNA from these fresh-frozen samples were hybridized to Affymetrix OncoScan arrays for SNP and CNA profiling. Whole-genome sequencing from 50 ng of DNA or more was completed on Illumina HiSeq 2000 sequencers. Full details on the patient cohort, whole genome sequencing protocols and SNP microarray protocols are given elsewhere (Fraser et al. Nature in press).

SNP Microarray Data Analysis

We identified CNV and SNP profiles using Affymetrix OncoScan FFPE Express 2.0 and 3.0 assays. To summarize, copy number segments were identified and annotated with RefGene (2014-07-15) and BEDTools (v2.17.0). Recurrent calls were filtered using a 75% threshold in the normal samples. CNA segments were generated using GISTIC2.0 (v2.0.22) and the average intensity of each segment was obtained from SNP arrays. gpure (v1.1) and ASCAT (v2.1) algorithms estimated cancer cellular purities using data from the SNP arrays. Full details are given in Fraser et al.

Whole-Genome Sequencing Data Analysis

WGS data was aligned and had somatic single nucleotide variant calls (SNV) calls for each tumour were previously generated (Fraser et al. Nature in press). Briefly, for each tumour, bwa-aln (v0.5-7) was used to align the tumour and normal FASTQ files against build hg19 of the human genome. These BAMs were then locally realigned and subject to quality-score recalibration using GATK (v2.4.9), followed by lane- and sample-level sample mixup checking and lane-level cross-individual contamination assessment using ContEst (v1.0.24530). SomaticSniper (v1.0.2) was then run on the aligned, recalibrated BAMs to generate predicted somatic SNVs. Full details are given in Fraser et al.

Somatic Subclonal Copy Number Assessment

Copy number aberrations (CNAs) were predicted from the whole-genome sequencing data using TITAN[21]. First, GC content and mappability files were prepared from the reference file using the BioConductor package HMMcopy and bowtie v(2.2.6). We referred to the practices outlined here: comgbio.bccrc.ca. Next, the Kronos (v1.12.0) pipeliner was used to preprocess the whole-genome data and run TITAN to generate the copy number calls. MutationSeq (v4.3.7) determined the heterozygous positions in the data using the known dbSNP sites from GATK. The GC and mappability files accounted for any biases in the data, prior to running TITAN. TITAN was run across an input range of one to five clusters, representing the exact number of subclones to be predicted. The most optimal set of parameters to be used was determined by the lowest S_Dbw validity index, and the resulting CNAs were used in all further analysis.

Phylogenetic Reconstruction of Tumours

To reconstruct the evolution of the tumour, we used the newly refactored cnv-int branch of PhylWGS[22], 2016 Jun. 21), in order to take into account both SNVs and CNAs. We used the parse_cnvs.py script to parse the TITAN optimal predicted CNA segments and tumour cellularities, and filtered any entries that were 1-bp TITAN CNAs. Further, these filtered CNAs and the high confidence SomaticSniper variant calls made on callable bases were inputted into the create_phylowgs_inputs.py script to generate PhyloWGS inputs. As a final CNA filter, we also removed any CNA entries generated that had a total read depth of 0. In addition, we annotated each SNV with the gene (if any) associated with the mutation as given by ANNOVAR (v2015-06-17)[23]. Using default parameters, PhyloWGS evolve.py script generated possible tree structures for each tumour. The JSON results were parsed to determine the best consensus tree, given by the largest log likelihood value, as well as the SNVs and CNAs associated with each subclone of the best predicted structure.

Phylogenetic trees were then aggregated across the cohort. The node numberings and edge connections in PhyloWGS trees were hierarchized by subclone cellular prevalence and thus not translatable across different samples with the same overall evolutionary trajectory. With the root node (normal population) labelled as 0, each consensus tree was "heapify" according to the following rules:
1. Nodes at depth i are labelled a lower number than all nodes at depth j, where j>i.

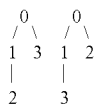

2. Trees are left-heavy.

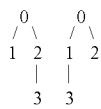

Notice that in the example above, the two tree structures were the same. For each individual tumour tree, we ensured that each node has at least 5 SNVs or 5 CNAs. Nodes that did not satisfy the criteria were: 1) merged with its parent node, if it has no siblings (its parent has no other child); 2) merged with its siblings; or 3) eliminated if it is the only direct child of the normal node. The eliminated node's children become the direct descendants of the normal.

Scoring Tree Structures

To quantify the subclonal diversity of each tumour sample by the number and abundance of subclones, we calculated the Shannon diversity index (H) (REF) by the equation $H = -\sum p_i \ln(p_i)$ where pi is the abundance of clone i in tumour. Clonal abundance is calculated using the CCF (cancer cell fraction) of each node, subtracted by the total CCF of its children, as to give the percentage of cells still belonging to the subclone in the tumour.

Classifying Mutations

Using the consensus trees generated by PhyloWGS, we classified mutations (both CNAs and SNVs) as occurring in the trunk or branch of the tree. Truncal mutations encompassed those that occurred between the root node (normal) and its only child node, while all others were classified to have occurred in branch.

Representative Tree Structures

We aggregated the patients based on their overall structure using the median rank product tree of tumours. For each patient, the product was calculated by multiplying the rank in terms of the number of SNVs, CNAs measured by total PGA, and tumour purity. Each condensed tree was represented by the median value. A 95% confidence interval was drawn around each node of the tree.

Subclonal Analysis of Driver Mutations

We identified recurrent coding SNV mutations and classified them as have occurred in trunk or branch. All SNVs assigned by PhyloWGS were filtered against blacklists of known sequencing artifacts and germline contaminants, and whitelists of recurrent COSMIC (v70) mutations (Fraser et al.) Nonsynonymous, stop-loss, stop-gain or splice-site SNVs were considered as functional (based on RefGene annotations). For each gene that was recurrently mutated at 2% or higher (with functional SNVs in more than 4 patients), we calculated the proportion of SNVs that have occurred in trunk. We used Fisher's exact test to check for significance of whether the gene was preferentially mutated in the trunk or in the branch.

For the non-coding SNVs (ncSNVs) assigned by PhyloWGS, we considered only those previously identified as recurrent ncSNVs (Fraser et al. Nature in press). We calculated the proportion of each recurrent ncSNVs that have occurred in trunk and used Fisher's exact test to check for significance.

The copy number aberrations (CNAs) as initially identified by PhyloWGS were assigned to have occurred in the trunk or branch. The CNAs for patients that had OncoScan data were further filtered by against those reported by the technology, retaining only the TITAN-predicted CNA that had overlapped. For patients that didn't have OncoScan data, we used the mean recurrence across the other patients in each chromosome. We compared the presence of truncal and branch CNAs across the patients and identified 13 groups of significantly different CNAs (proportional test; multiple correction using FDR; q≤0.01). Groups were determined by their genomic location on either chromosome and more specifically, chromosome arm. Bins that were within 3 Mbp of each other were considered as the same group.

Consensus clustering was applied separately to the trunk and branch CNA profiles using the ConsensusClusterPlus package (v1.24.0), customized to include the Jaccard distance metric (trunk: distance=Euclidean, pItem=0.8, finalLinkage=Ward.D2, innerLinkage=Ward.D2; branch: distance=Jaccard, pItem=0.8, finalLinkage=Ward.D2, innerLinkage=Ward.D2)[24]. The optimal cluster number was selected by minimizing the proportion of ambiguous clustering value[25].

Pathway Analysis of Differentially Enriched CNAs

The genes involved in the 13 groups of significantly different CNAs were analyzed further for pathway enrichment. Using gprofileR (v0.6.1) in R (v3.2.5)[26], all statistically significant pathways were obtained from default parameters and the data sources Gene Ontology (Biological Process, Molecular Function, and Cellular Component), KEGG and Reactome. Pathways that involved more than 700 or fewer than 5 genes were discarded[27].

To identify pathways that were significantly differentially affected in the trunk and branch, we used Fisher's exact test to assess whether the gene-set was more frequently affected by trunk or branch CNAs and label permutation to determine their significance[27]. For each patient, the trunk and branch CNA profiles were separately used to determine the gene-sets affected. A pathway was considered to be affected if the CNAs implicated at least one gene belonging to the gene-set. As the CNAs belonged to either trunk or branch, the location status of the set of pathways affected were respectively classified as trunk or branch. After initial assignment, we permuted the location status of pathway sets 1000 times so that the CNA events were independent of location assignment. The P-values generated from Fisher's Exact Test through the iterations were used to build the null hypothesis distribution and all pathways with adjusted Q-values of greater than 0.05 are considered not significant. According to this threshold, 33 CNA affected gene-sets were found to be enriched in either trunk or branch.

Subclonal Analysis of Kataegis

To quantify where and when kataegis events occurred, we used the sliding window binomial test approach as reported in Fraser et al. Each subclone of every patient was considered separately, with all of its post-filter SNVs assigned by PhyloWGS in the consensus tree, as to pinpoint where the kataegis events occurred in tumour evolution. A rainfall plot with the x-axis as SNV position and the y-axis as the log transformed inter-mutational distance was generated to represent all of the SNVs in all of the patients that had at least one kataegis event, with the SNVs involved in the events highlighted using their timing of occurrence.

Incorporation of Trinucleotide Mutation Signatures

First, we separated mutations into 96 types based on their trinucleotide context. Then, we used mutation population frequency (PF) as an estimate of the relative order in which mutations occurred in the tumor, assuming that mutations with higher frequency occurred earlier. We sorted mutations by PF in decreasing order, where PF is estimated as a mean across trees from the PhyloWGS analysis.

Population frequency can be viewed as pseudo-time of mutation occurrence. We divided mutations into bins of one hundred and considered each bin to correspond to one time point. To make the exposure estimation more robust, we merged the bins of 100 into bins of 400 in a sliding window manner.

To estimate signature exposures, we used a set of 30 signatures from COSMIC (cancer.sanoer.ac.uk)[28]. Signatures are represented as multinomial distributions over 96 types of mutations. We fit a mixture of multinomials in each bin. Obtained mixture coefficients correspond to exposures of the mutational signatures that generated mutations in this bin. We evaluate uncertainty by bootstrapping set of mutations and recomputing exposure estimates 20 times. The standard deviation of the exposures at each timepoint was used as the estimated standard error and plotted as error bars.

Time points when signature profiles change substantially represent loss or gain of different mutational processes. To find a new change point, we iterated through all time points and recomputed mixtures of multinomials in time slices formed by a potential change point. A point with maximum likelihood is considered a new change point. We used the Bayesian Information Criterion to determine the optimal number of change points. As mixtures of multinomials are computed over all mutations enclosed between adjacent change points, exposure trajectories obtain piecewise constant shape.

Not all of the signatures are active in the tumor at the same time. Active signatures may depend on cancer type, environment, etc. We first fitted all 30 COSMIC signatures, and then chose a subset of six signatures most active in our samples (namely S1, S3, S5, S8, S9 and S16). We re-fit the mixture model with the selected set of signatures only and used this set of signatures for our further analysis. Using these selected signatures, exposures in mutation bins were plotted against 1Φ scale. Signatures that did not reach 20% at any time-point were excluded from the visualizations.

To assess whether the trinucleotide context-specific distribution of mutations changed between trunk and branch within each sample, we used Pearson's $\chi^2$ test. Trinucleotide contexts were collapsed on the 5' base if any of the full categories contained fewer than 3 SNVs.

Subclonal Tree Correlations

We used Spearman's ρ to test for associations with age at diagnosis, PSA, clinical Gleason Score, T-category and ERG fusion status. We compared these to a set of tree features comprising PhyloWGS subclone counts, tree depth, proportion of SNVs in trunk, proportion of CNAs, in trunk, Shannon Index, total PGA, PGA accumulated in trunk and kataegis events. Additional associations were tested amongst these tree correlates as well as tumour cellularity. Only polyclonal samples were analyzed as they have both a trunk and a branch. CNAs Trunk and SNVs Trunk refer to the proportion of CNAs and SNVs in the trunk, respectively. PGA Overall refers to the total PGA in the sample while PGA Trunk refers to PGA in the trunk node only.

Microarray Sensitivity

We split the filtered TITAN CNAs into trunk and branch ones, creating separate gene by patient matrices. For each patient we then considered what proportion of the genes with a TITAN CNA also had a CNA reported by OncoScan. We tested for differences between the proportion of trunk CNAs detected and the proportion of branch CNAs detected with a Mann-Whitney U-test.

Survival Analysis

The tumours were arranged into two distinct clonality groups: monoclonal tumours only derive one clonal population in its evolution, while polyclonal includes the remainder, with at least one subclonal population. We assessed differences in outcome by fitting a Cox proportional hazard regression model, reporting the P-value from the Wald test. Multivariate analyses were carried out to correct for clinical variables (clinical Gleason Score, clinical T-category and pre-treatment PSA), and the power to detect subclones (reads per cancer cell, number of SNVs and number of CNAs). The proportional hazards assumption was verified by examination of the Schoenfeld residuals and, for multi-variate analyses, global Pearson's $\chi^2$ tests. Primary outcome was time to BCR, defined to be a PSA rise of ≥2.0 ng/mL above the nadir PSA for patients who underwent image-guided radiotherapy. For patients who underwent surgery, BCR was defined as two consecutive post-surgery PSA measurements>2.0 ng/mL (backdated to the date of the first increase). If a patient had successful salvage radiation therapy, the patient was not considered to have a BCR. If PSA continued to rise after salvage radiation therapy, BCR was backdated was backdated to the first PSA measurement>0.2 ng/mL. If a patient received other salvage treatment (such as hormonal therapy or chemotherapy), this is considered a BCR.

Scoring Biomarker Signatures

The proportion of the genome altered (PGA) was calculated for each clonal population in a patient's tumour, where every population harbours all of the CNAs that have occurred in its evolutionary history. Trunk PGA was calculated from trunk CNAs, while branch PGA was calculated from the CNAs that have occurred between the clonal node and the most altered subclonal node. PGA was calculated by summing the total number of bases covered by the CNAs and divided by the total size of the whole genome. We used the previously validated at-risk threshold of 7.49% PGA: patients below this value are predicted to have good prognosis, and patients equal to or above it are predicted to have poor prognosis[13].

To confirm the PGA results, we also used a validated prognostic 100-locus CNA signature for localised prostate cancer to assess the risk of each patient (Lalonde et al. European Urology in press). This signature was applied to each clonal population in a patient's tumour in the same way as for PGA: the patient risk score resulting from only the clonal node is the trunk risk score, while the gain in risk score between the clonal and the subclone with the highest risk is defined as the branch risk score. We retained the published and validated at-risk threshold for this signature of 0.5, with scores lower than this indicating good prognosis and those equal to or higher predicting poor prognosis. We used Cox proportional hazard models and area under the receiver operator curve to assess differences in biomarkers applied to different nodes.

Data Visualization and Reporting

Plotting was performed in the R statistical environment (v3.2.5) using the lattice (v0.20-34), latticeExtra (v0.6-28) and BPG (v5.3.4) packages. Figures were also compiled using Inkscape (v0.48) and Cytoscape (v3.4.0). Point estimates for the mean were reported along with a 95% confidence interval for the population mean. Unless otherwise stated, all statistical tests are two-sided. In FIG. 1, the representative tree for each tree structure was selected by calculating the rank product of the number of SNVs, PGA, and tumour purity. The tree with the median rank-product was selected for visualization. All trees were generated, but data not shown.

Results and Discussion

The Subclonal Architecture of Intermediate-Risk Prostate Cancer

Figure 7:
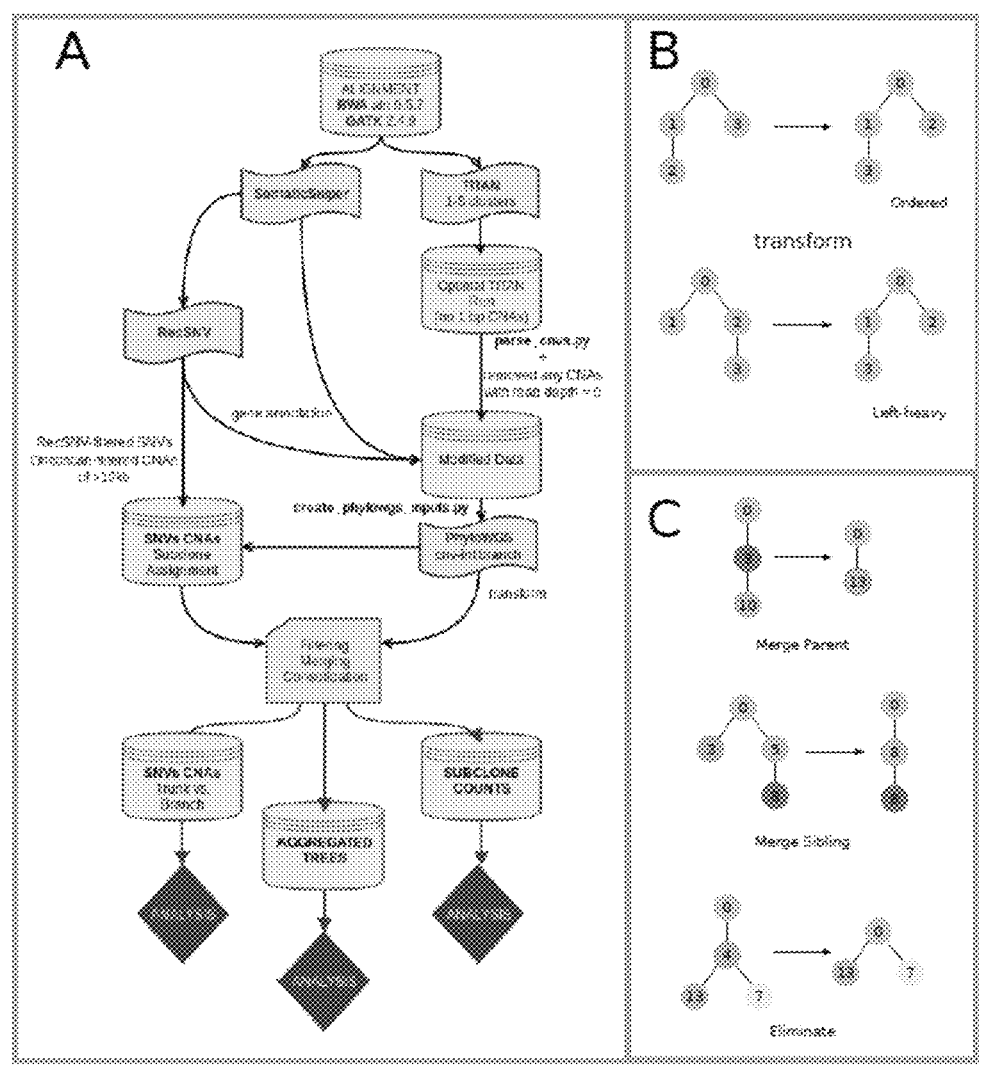
FIG. 7 shows a reconstruction workflow. (A) Summarizes the analysis workflow, starting from raw sequencing data and ending with processed and annotated trees. (B) Intermediate processing step in which the PhyloWGS reconstructed trees were aggregated across the cohort. Nodes are initially numbered according to what PhyloWGS calls them, and then transformed to a hierarchical structure. (C) Intermediate processing step that determines if a node has sufficient number of mutations. Nodes are labeled by the number of mutations they have and colour-coded based on the subclone they arise from. This represents cases when a node is merged with its parent, merged with its sibling and when it can be eliminated.
Figure 8:
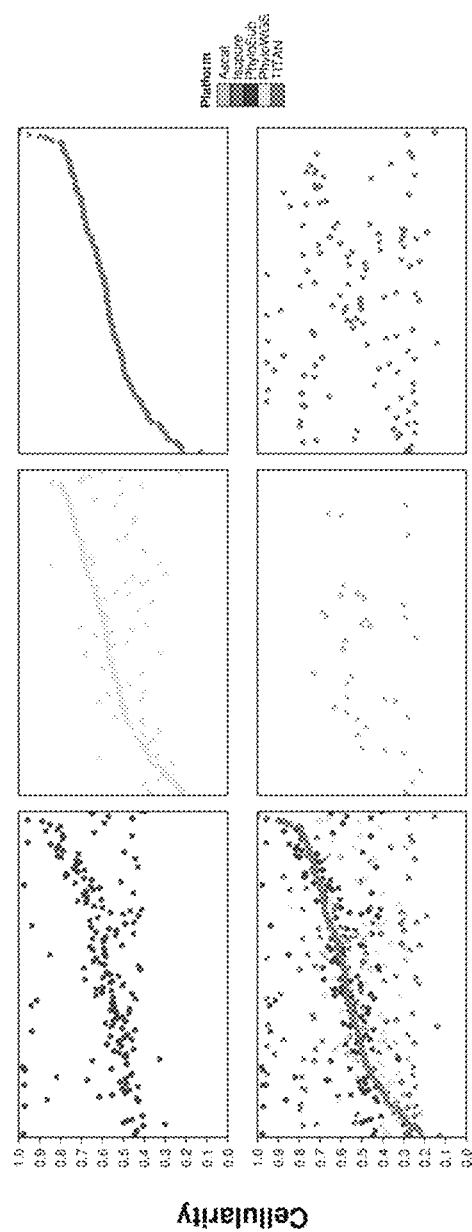
FIG. 8 shows a cellularity comparison. Cellularity estimates from PhyloWGS, PhyloSub, TITAN, Ascat, and Isopure. The bottom left shows an overlay of all methods while the other panels show different estimation methods. Each dot shows the estimate for a sample. Samples are ordered by TITAN cellularity estimates.

To understand the subclonal architecture of localized prostate tumours, we studied 200 tumours from patients diagnosed with clinically intermediate-risk disease—the largest clinical sub-group (data not shown). Patients were treated with either surgery or radiotherapy, and samples of the index lesion and paired normal (blood) references have been whole-genome sequenced (WGS) previously (Fraser et al. Nature in press). For each patient, we reconstructed their subclonal profile by identifying when mutations occurred. Somatic single nucleotide variants (SNVs) called by SomaticSniper together with copy number aberrations (CNAs) predicted by TITAN were characterized by PhyloWGS on an evolutionary tree (data not shown). We initially predicted subclone compositions using TITAN, and compared and contrasted with the reconstructions made by PhyloWGS and PhyloSub (FIG. 7). We confirmed that subclonal reconstruction was not biased by study (FIG. 8A) and showed high power (FIG. 8B). Of these 200 tumours, 41 (20.5%) were identified as having only clonal mutations (termed monoclonal)—at least given our sequencing depth and the single spatial region of the tumour sequenced (FIG. 1A, FIG. 8C, and data not shown). Another 71.5% had evidence of multiple tumour populations originating from a single ancestral clone (termed polyclonal). The remaining 8% showed apparent poly-tumour character, suggestive of patients with multiple independent primaries as observed in multi-region sequencing studies. However, reconstruction of poly-tumours from single-region sequencing is computationally unreliable and we therefore exclude these 16 tumours from all downstream analyses and focus on the 184 tumours with reliable reconstructions. Annotated trees for all tumours were generated but not shown.

Figure 9:
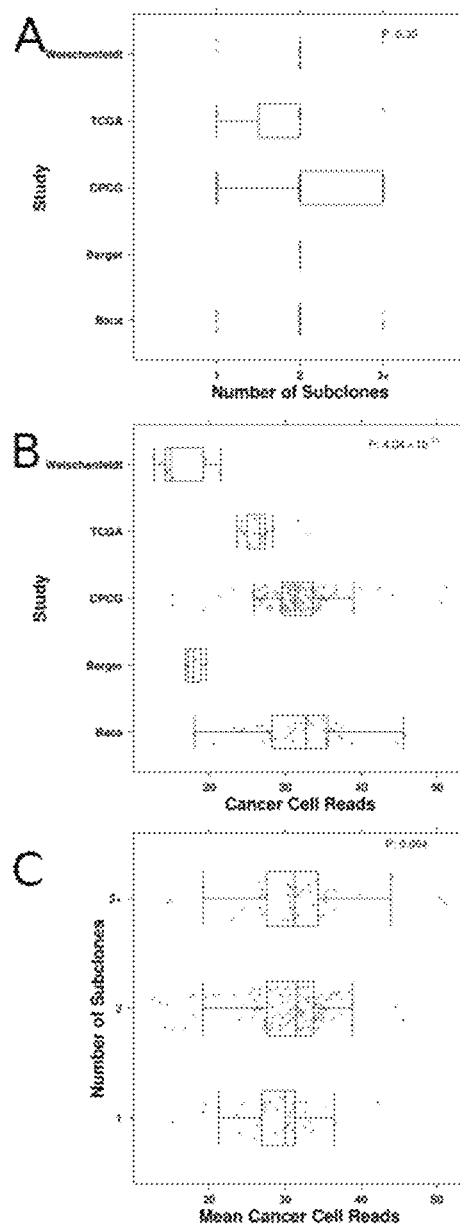
FIG. 9 shows a coverage by study. (A) shows the number of subclones detected by study. (B) gives the sample coverage for cancer cells in each study, corrected by ploidy to give reads per chromosome. (C) shows the distribution of per-tumour-coverage by the number of subclones detected. P values from a Kruskal Wallis test are shown in all three plots.
Figure 10:
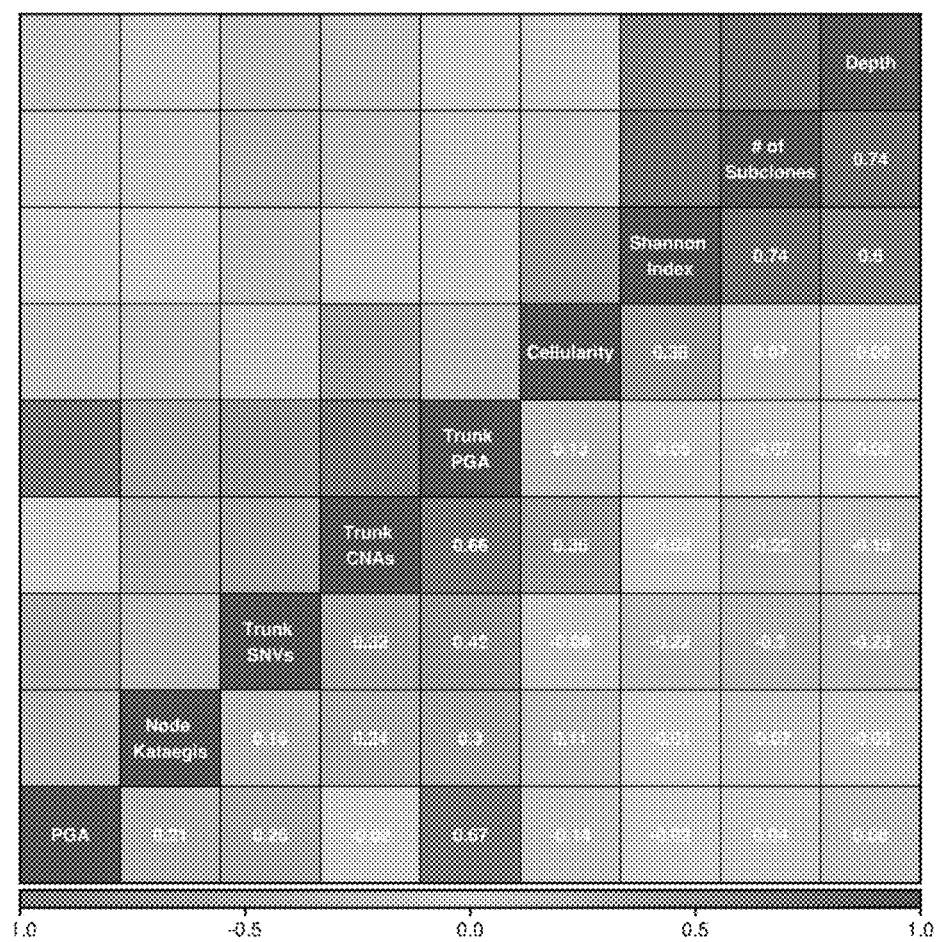
FIG. 10 shows phylogeny interactions. Correlations between tree characteristics using Spearman's p.

The key clinical variables that are used to stratify prostate tumours are pre-treatment serum levels of prostate specific antigen (PSA), tumour grade (Gleason Score) and tumour size (T-category). Additionally, ~50% of tumours harbour fusion of ETS-family genes. We tested each of these variables for association with characteristics of the tumour phylogenies (FIG. 1B, and data not shown). As expected, tumours with elevated Gleason Score showed elevated proportions of the genome copy-number altered (PGA), both overall and in their trunk, and higher proportions of SNVs in their trunk (Fraser et al. Nature in press). We also tested each of the interactions within the phylogeny characteristics and showed the expected strong correlations (FIG. 9). Tumours driven by ETS fusion genes tended to have a lower proportion of somatic SNVs in their trunks and to be depleted for kataegic events, despite the cohort having more kataegic events overall in trunk (FIG. 10), perhaps reflecting the effects of this tumour-initiating mutation.

Mutational Timing and Mutational Processes

Figure 2:
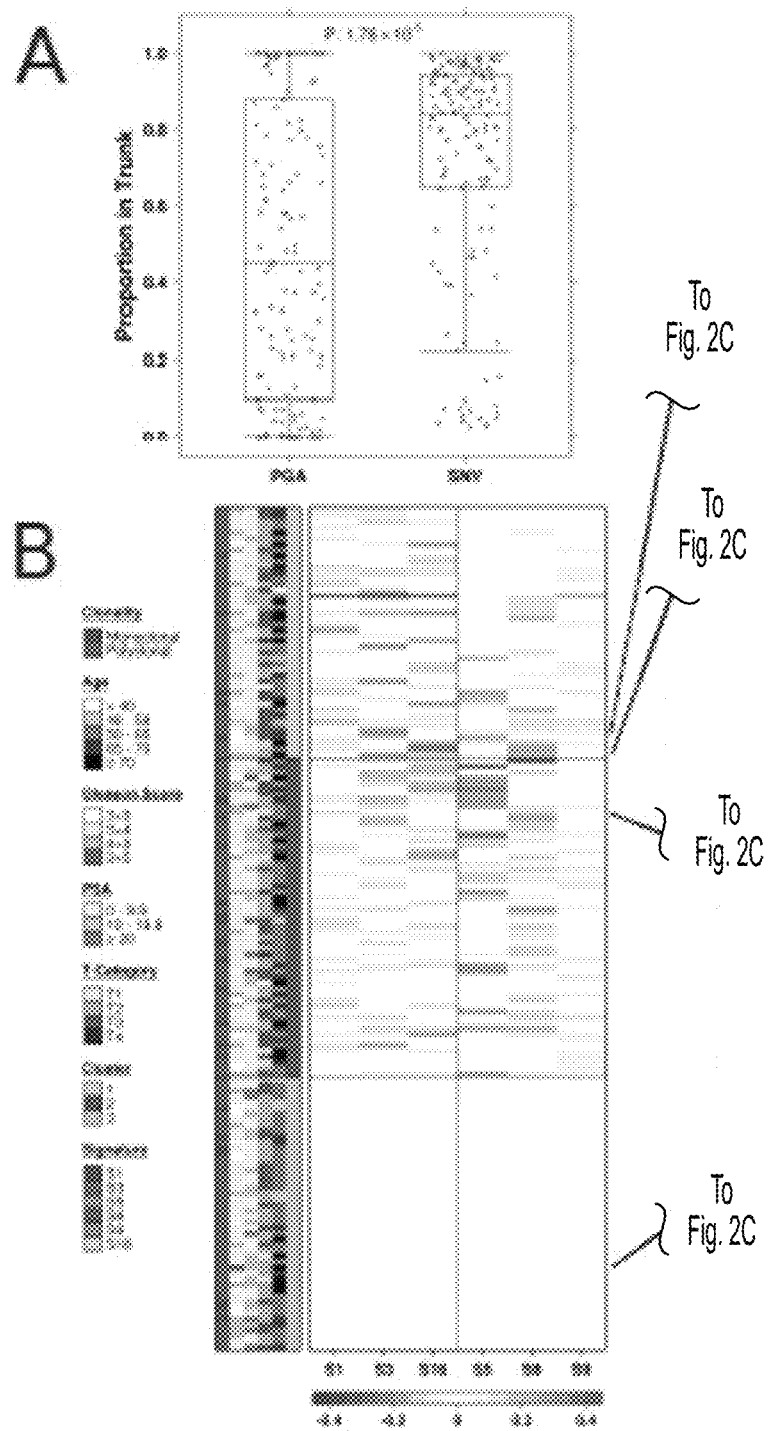
FIG. 2 shows Evolution Mutational Processes in Prostate Cancer. The acquisition of mutations along a tumour evolution is differentiated in (A). Differences in the proportion of SNVs and CNAs, measured by PGA, emerging from trunk are tested with a Mann-Whitney U-test. The six most prevalent signatures in our cohort and their exposure changes are displayed in (B). Signatures are clustered into two groups and samples are ordered by their signature changes. Exemplars with varying exposures are chosen for (C). Changes are split into trunk and branch panels for polyclonal tumours with enough SNVs in both trunk and branch. Change-points are highlighted using vertical black lines.

We next sought to understand the mutational processes underlying prostate tumourigenesis, and how they change over the course of tumour evolution. We first compared the types of mutations present in the trunk of tumours and those that occur in their branches. An average of 48.7%±6.57% of copy number variation (as assessed by PGA) occurs in the trunk of a tumour, with the remainder occurring subclonally (FIG. 2A). By contrast, most somatic point mutations (72.6%±4.86% of SNVs) occur in the trunk ($p=1.76\times10^{-5}$; Mann-Whitney U-test). Thus the initial evolution of prostate cancer involves accumulation of a large number of SNVs (with most likely as passenger mutations) while the later clonal divergence involves significant copy number changes.

Figure 2C:
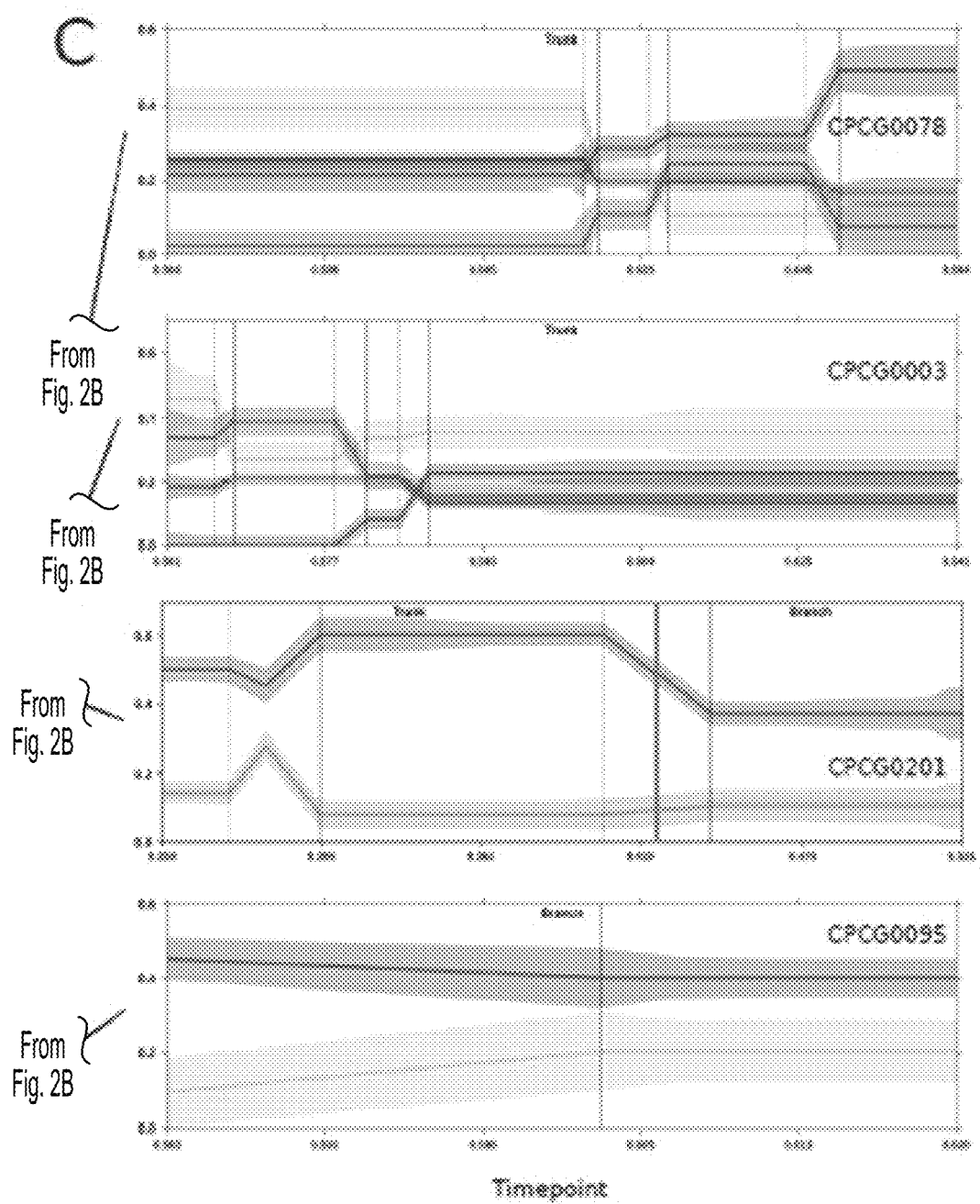
Figure 11:
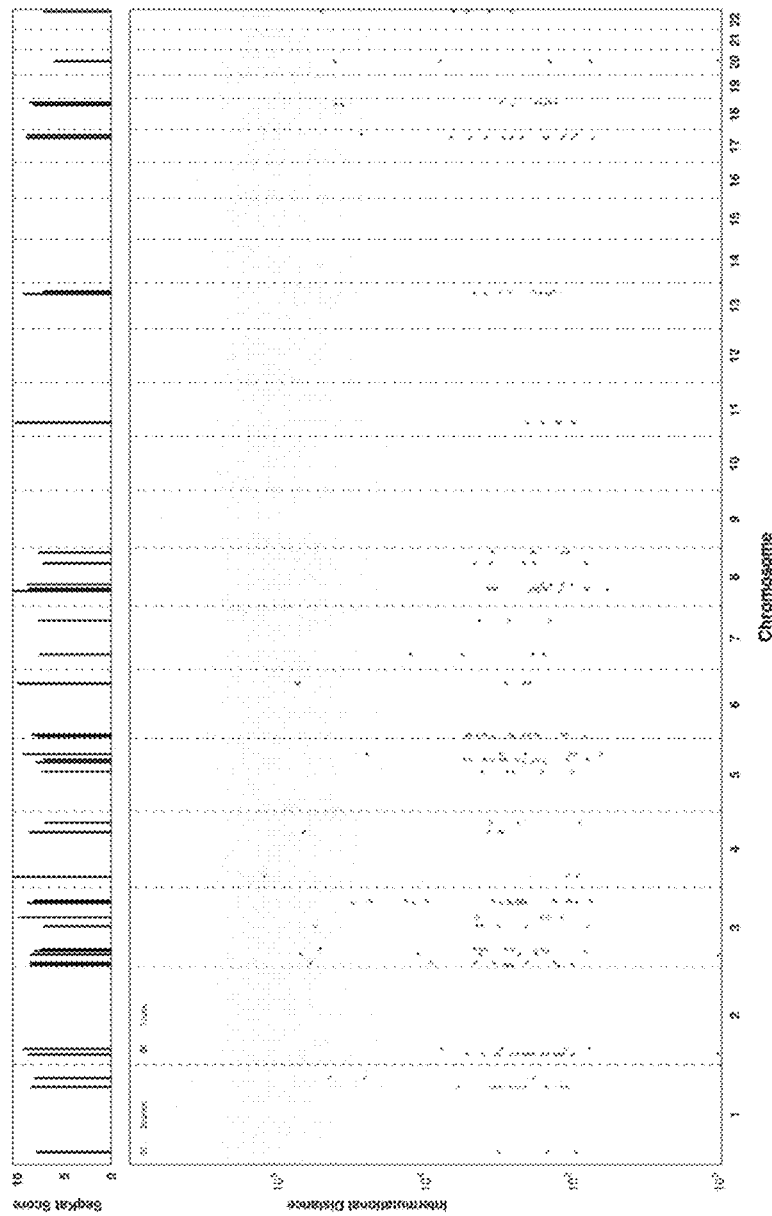
FIG. 11 shows kateagic events. Kataegic events across all samples. Each dot represents a SNV, and the colouring specifies whether an SNV is part of a kataegic event in trunk or branch. Within a kataegic cluster of mutations, inter-mutational distances are calculated. Kataegis score measures the significance of deviation, from expected, within these clusters (outlined in detail in Fraser et al.).
Figure 12:
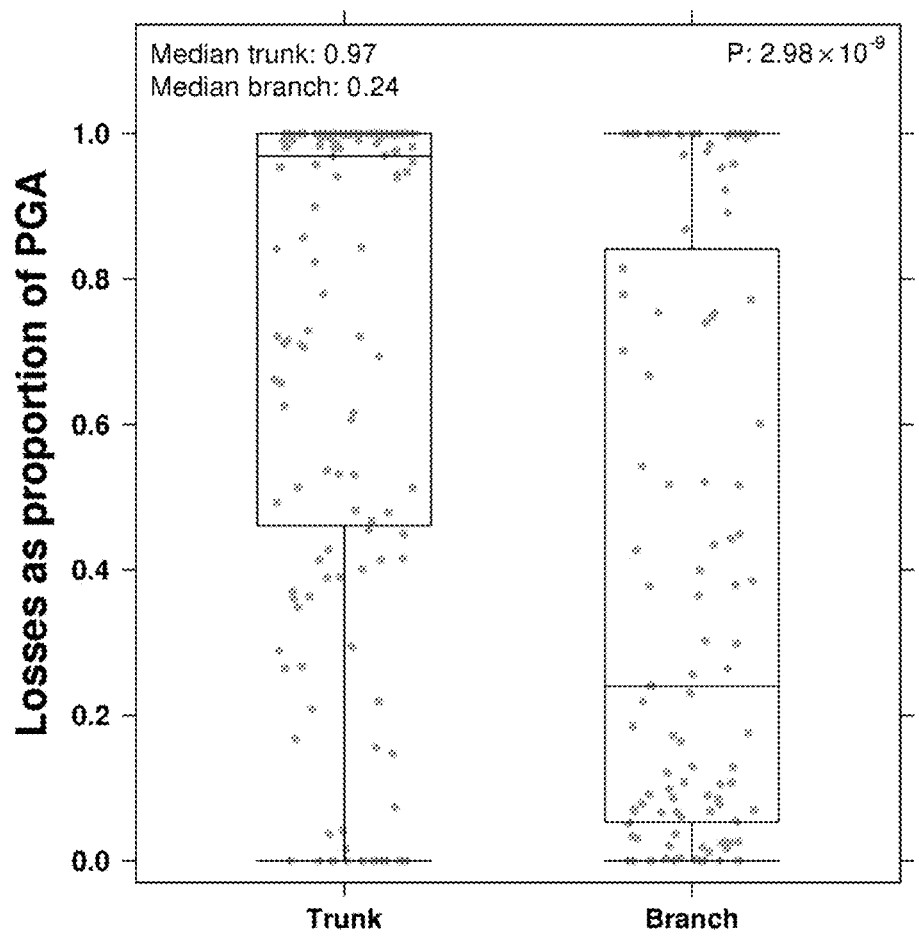
FIG. 12 shows losses as proportion of CNAs. Proportion of 1 Mbp bins that contain a CNA that are predominantly losses: an estimate of loss-only PGA. P-value from a Mann-Whitney U-test is shown.

To understand the mutational processes driving this early accumulation of somatic SNVs, we sorted SNVs by their population frequency and decomposed them into COSMIC signatures at different time-points of tumour evolution. For each patient, we estimated mutational timing using the average population frequency across all the trees generated by PhyloWGS. Mutations were binned and COSMIC signatures were fitted into each bin, using bootstrap methods to estimate exposures. We defined new time points by detecting changes in the multinomial mixture and chose the top 6 signatures most prevalent in our samples (FIG. 11). The overall gain or loss in signature exposure showed diversity across subclonal populations (FIG. 2B, FIG. 12). Changes in exposure were plotted across calculated time points, and signatures fewer than 20% were omitted. Signature changes accumulated across subclonal populations were indicated, as shown in the exemplars (FIG. 2C).

The Molecular Hallmarks of Subclonality

Figure 3:
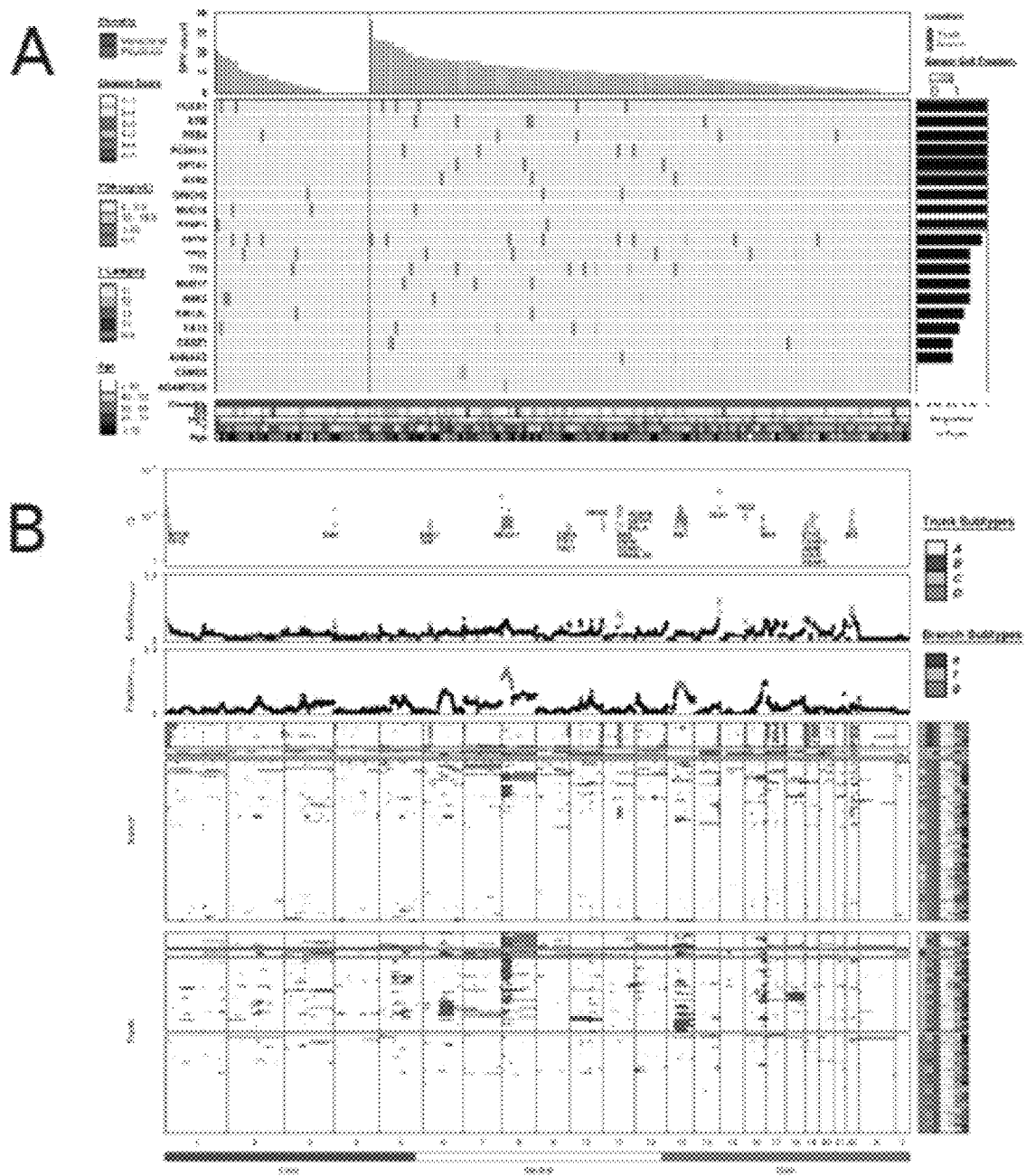
FIG. 3 shows Evolution of Driver Mutations. The timing of driver mutations in prostate cancer is shown (A) and (B). Mutations are classified as trunk or branch according to their time of occurrence. Trunk mutations define the clonal node from the normal population, while branch mutations develop after clonal establishment. (A) Patients are ordered by total number of functional mutations, while the driver SNVs are sorted by proportion defined as trunk and overall frequency. The cancer cell fraction measures the proportion of the tumour subpopulation that harbours the mutation. (B) CNA profiles of 184 prostate tumours, split by CNA occurrence in trunk and branch. Red indicates gain; blue indicates loss; rows represent patients; columns represent 1 Mbp genomic bins. Patients are clustered by their trunk and branch CNA profiles. The top two plots reflect trunk-branch differences in CNA frequency, showing the statistical significance (top plot, Q-value) and effect-size (difference in frequency between trunk and branch, F Trunk–F Branch). Key altered genes (Pearson's $\chi^2$ test, FDR adjustment) within these regions are labeled. (C) and (D) show the co-occurrence of trunk and branch subtypes, respectively.
Figure 3:
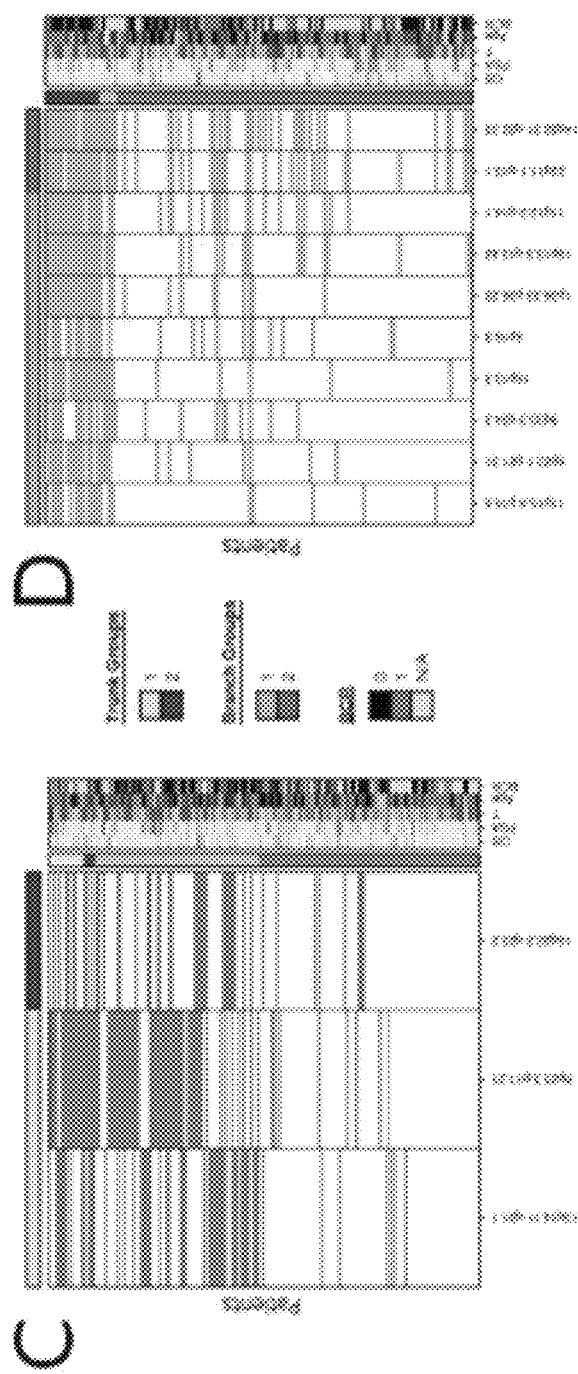
Figure 13:
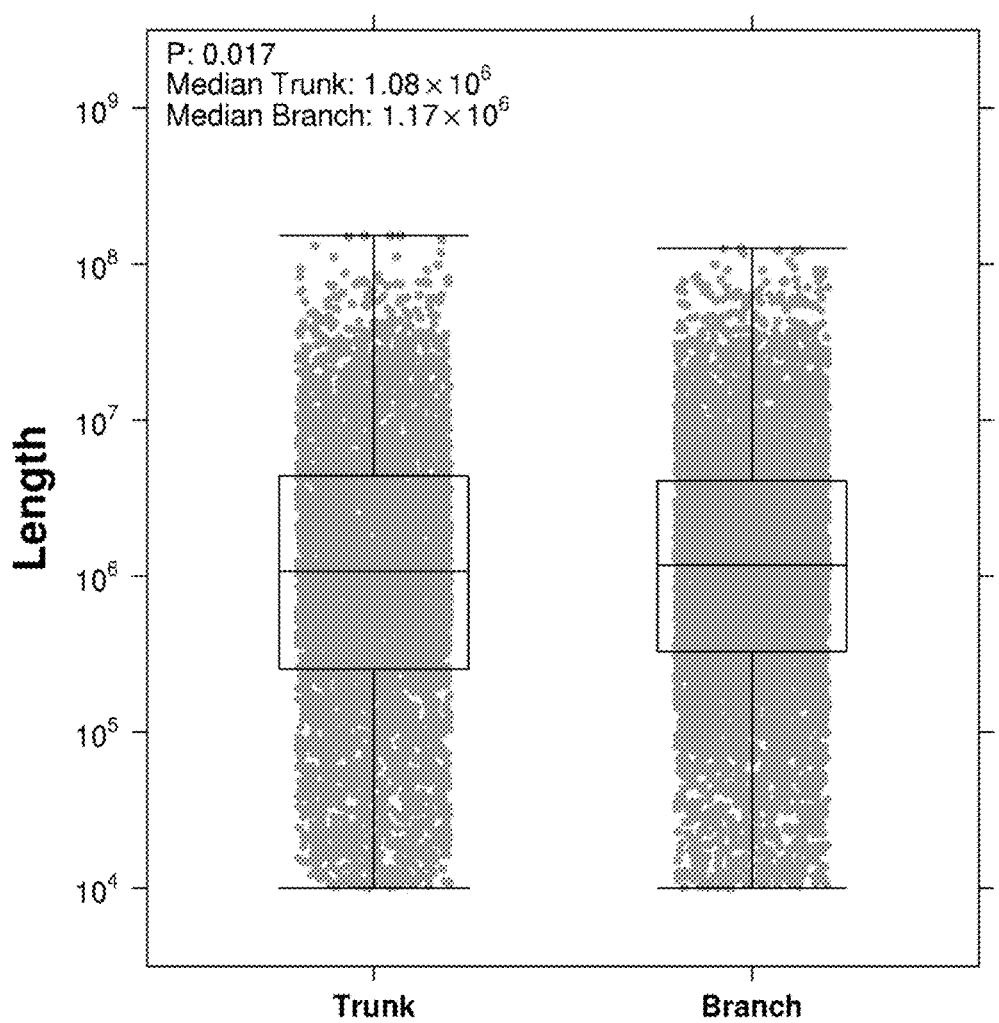
FIG. 13 shows size comparison of CNAs. Comparison of CNA lengths in trunk and branch. P-value from a Mann-Whitney U-test is shown.

We hypothesized that the different mutational processes present in the trunk and branch of prostate tumours would reflect distinct sets of driver mutations occurring in these two different phases of tumour evolution. We considered all genes (data not shown) recurrently affected by functional somatic SNVs (genes with nonsynonymous, stop-loss, stop-gain and splice-site SNVs in at least 2% of patients). Some mutations were strictly clonal (i.e. found in the trunk of the tumour), including the well-known prostate cancer genes FOXA1 and ATM (FIG. 3A, and data not shown). By contrast, some genes were observed to be mutated both clonally and subclonally (e.g. TP53 and SPOP), and others only subclonally (e.g. CSMD3). Similarly, we identify specific recurrent non-coding SNVs to have trunk vs. branch bias (FIG. 13). We similarly considered the clonality of somatic CNAs, and again identified specific mutations strongly enriched in the trunk of the tumour (data not shown). These include the hallmark NKX3-1 deletion present in more than a quarter of all prostate tumours (with 57/200 NKX3-1 deletions in the trunk vs. 26/200 in the branch; $p=2.16\times10^{-4}$; chi-squared test). Other clonal mutations included deletion of RB1 (38/200 in the trunk vs. 10/200 in the branch; $p=3.26\times10^{-5}$; chi-squared test) and deletion of a locus on chromosome 16 that included deletion of the tumour-suppressor MAF, which is linked to ETS-rearranged tumours[11]. An additional set of CNAs were identified to be recurrent subclonally (FIG. 3B, and data not shown). These include: mediators of cellular response and signaling (e.g. MTOR, TP73, HRAS); regulators of growth and apoptosis (e.g. BAK1, TNF1, BAD, BID); and other cancer driver genes (e.g. CCND1, CCNE1, JUNB, TSC1, TSC2, KEAP1).

Figure 14:
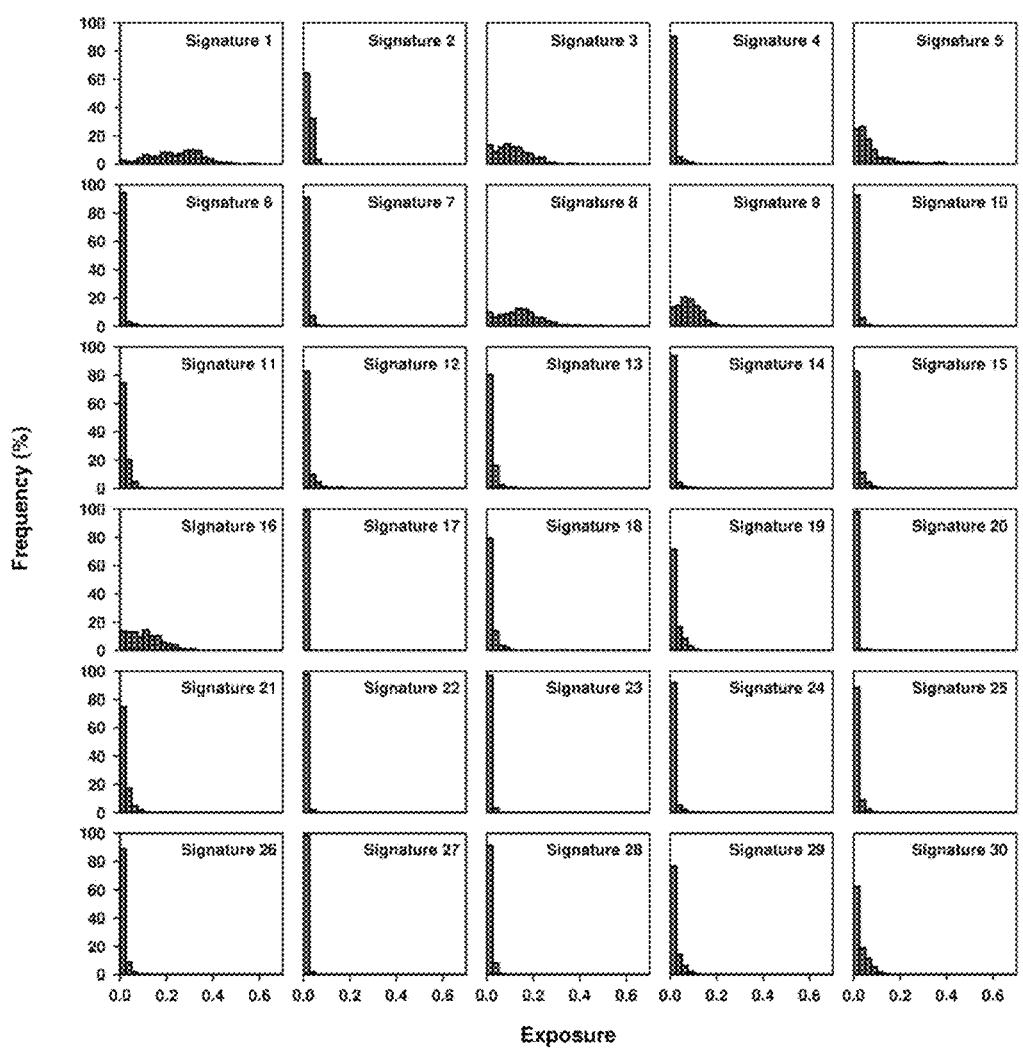
FIG. 14 shows signature contributions. Frequency of exposure level per signature, across all time-points in samples with more than 600 SNVs.
Figure 15:
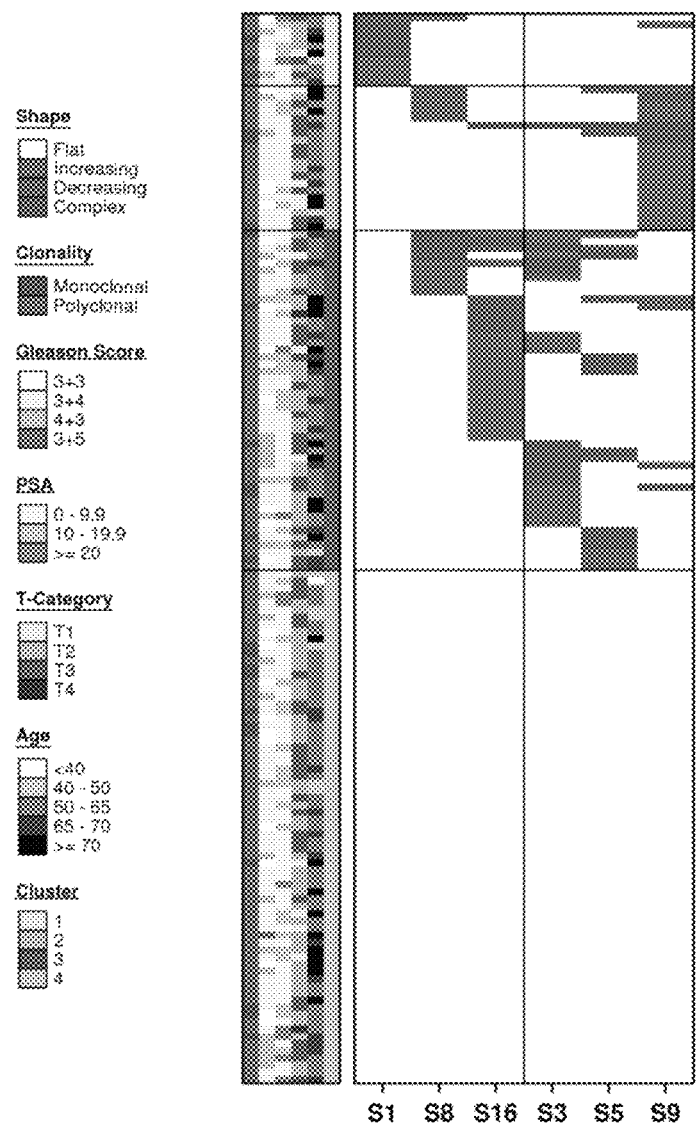
FIG. 15 shows signature shapes. Shape of each signature by sample, as characterized by change-points with non-overlapping error bars. Patients were clustered using consensus clustering, and sorted by signature shape within each cluster.
Figure 16:
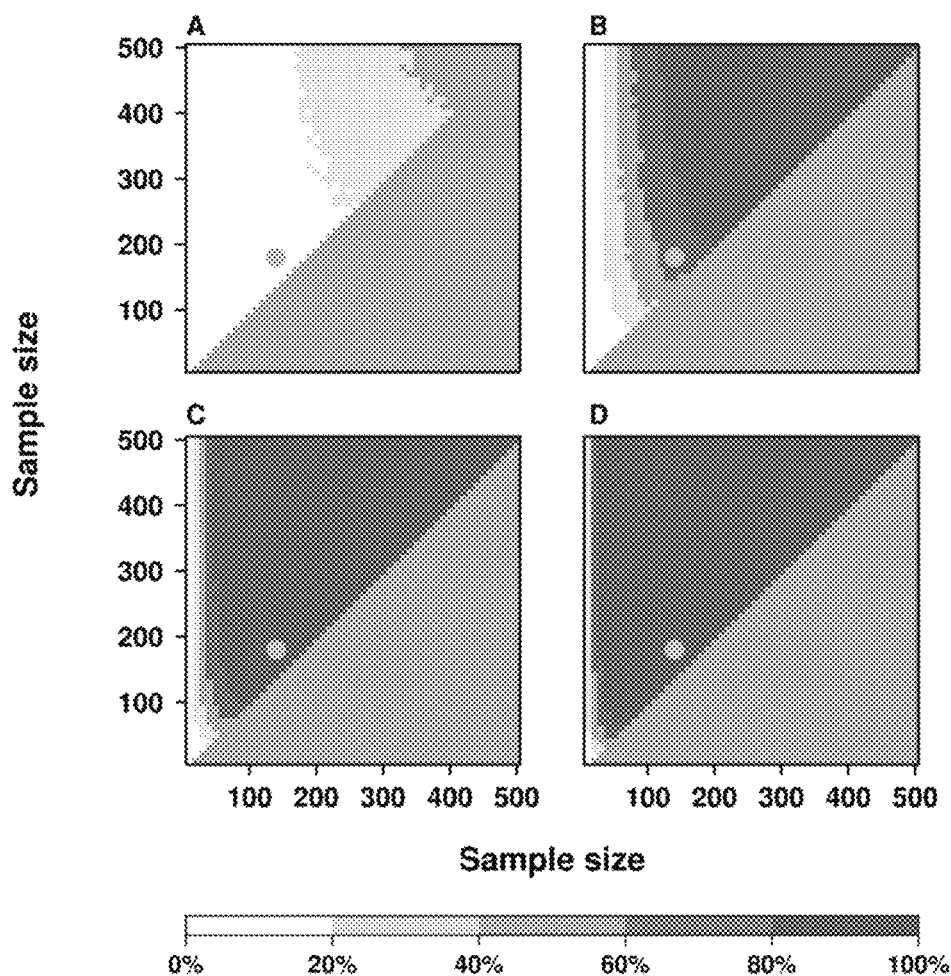
FIG. 16 shows power analysis of coding SNVs. Power analysis for tests of whether coding SNVs occur preferentially in trunk or branch, based on Fisher's exact test and Bonferroni correction for 20 tests. (A)-(D) show effect sizes 0.2, 0.4, 0.6, and 0.8, respectively. The orange dots indicate our sample size, and the background colour shows the power.

Pathway analysis revealed that genes found in significantly differentially mutated CNAs are involved in the retinoic acid receptor signaling, apoptosis, tumor necrosis factor activity, and interestingly, viral carcinogenesis. (data not shown). Indeed monoclonal tumours have longer telomere lengths than polyclonal tumours ($p=4.67\times10^{-3}$; Mann-Whitney U-test) (FIG. 14A), leading to characterization of branch patient subtypes. Trunk patient subtypes clustered along the strongly enriched mutations in trunk (FIG. 3C, FIG. 14B, and data not shown). Mutations in branch distinctly identified different patient subtypes, distinguished by their enrichment in branch CNAs (FIG. 3D, and data not shown) and telomere lengths (FIG. 14C; $p=1.12\times10^{-2}$; Kruskal-Wallis test). The trunk and branch patient subtypes are independent (FIG. 15), but generally overlap with those reported from previous microarray studies of large cohorts. In particular one of the branch subtypes, e, replicates a previously described CNA subtype with recurrent subtelomeric amplifications on multiple chromosomes (Fraser et al. Nature in press; FIG. 16A-C). These patients harbour shorter telomeres than the rest of the cohort (FIG. 16D) and harbour amplifications of both TERT and DNA methyltransferase 1 (DNMT1; FIG. 16E-F) which both regulate telomere length. These data suggest a novel, as-yet uncovered DNA damage or repair mechanism underlying this subclonal CNA subtype.

The Clinical Relevance of Tumour Subclonality

Metastatic prostate tumours harbour large numbers of spatially co-segregating subclones, with strong plausible therapeutic relevance. We assessed whether subclonality is associated with aggressive disease even in localized prostate cancer, when therapy can be curative. Patients whose tumour sample showed no evidence of multiple sub-populations showed significantly superior outcome to those whose tumours were polyclonal (FIG. 4A, HR=4.6, 95% CI: 1.4-14.8; $p=1.16\times10^{-2}$; Wald test). As a prognostic biomarker, clonality compares favourably to the very best tissue-based prognostic tests available (Lalonde et al. European Urology in press,[13-18]). These survival differences persist even after adjustment for the clinical prognostic factors pre-treatment PSA, clinical Gleason Score and clinical T-category (and data not shown). These data demonstrate that subclonal heterogeneity directly predicts clinically aggressive disease.

Figure 4:
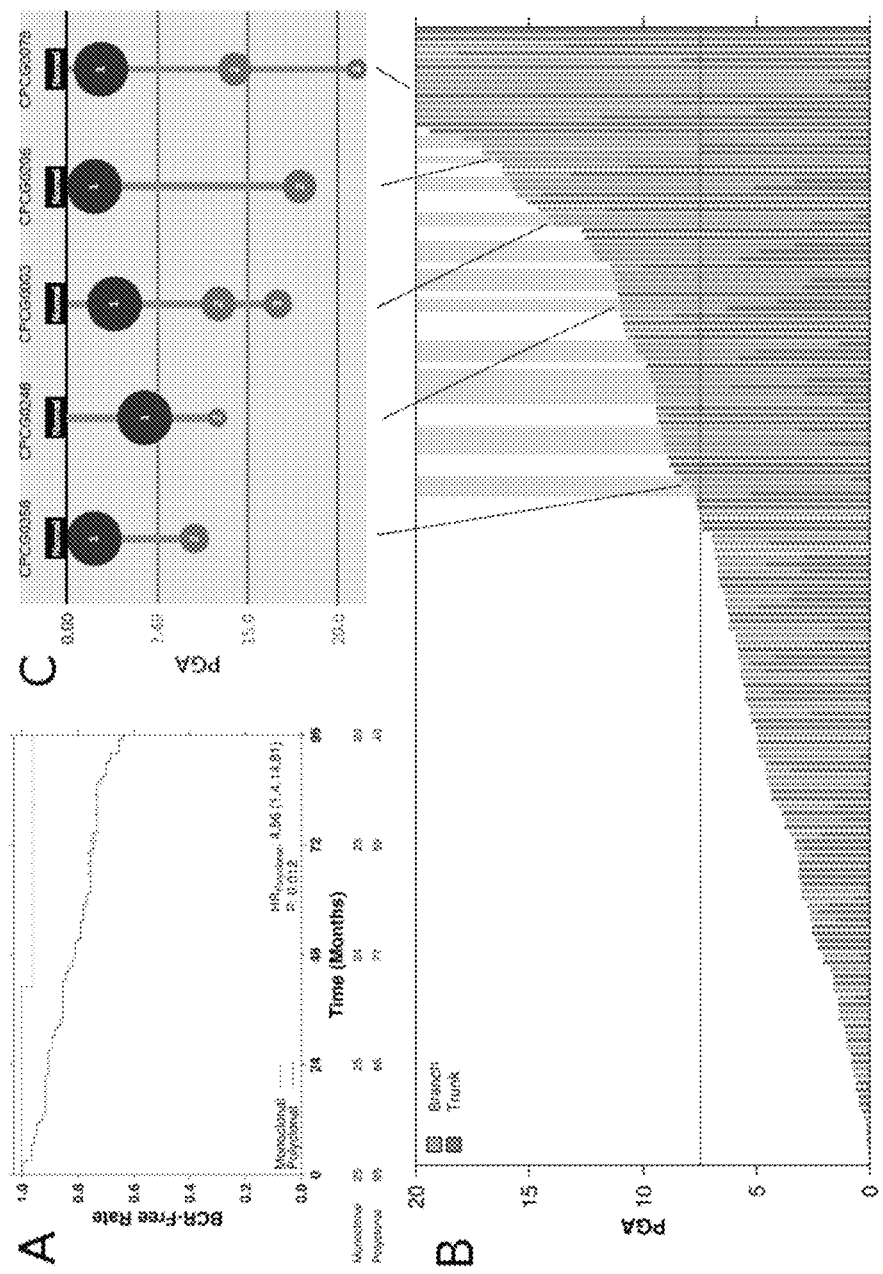
FIG. 4 shows the Clinical Relevance of Subclonality. Patient survival outcome between monoclonal and polyclonal samples is displayed in (A). Univariate modelling was carried out with a Cox proportional hazards model. Hazard ratio (HR) and Wald test p-value are shown. Patients are ordered by their total risk as assessed by PGA, shown in (B). The red line divides the low-risk (<7.49% PGA) from the high-risk (≥7.49% PGA) patients. Bars with a grey background indicate patients that are pushed to being high risk when considering CNAs that occur in their subclonal populations. Exemplars of these cases are shown in (C). Red outlines the turning point in which the patient becomes high risk.
Figure 17:
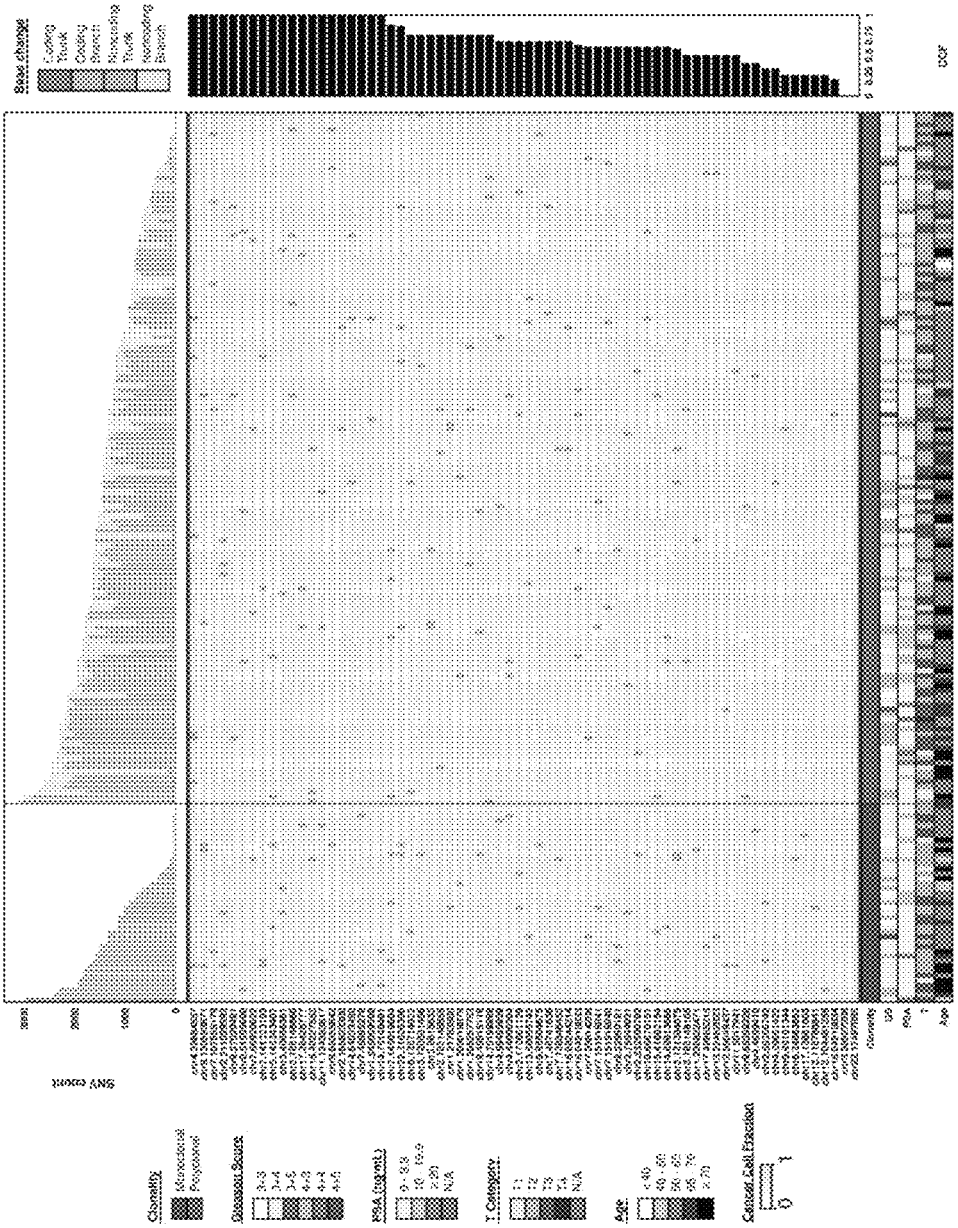
FIG. 17 shows subclonal non-Coding SNVs. Non-coding SNVs previously identified as recurrent (Fraser et al. Nature in press) were classified as trunk or branch. Samples are ordered by tree-type and the total number of SNVs (both coding and non-coding). Non-coding SNVs are sorted by their proportion of occurrence in trunk.
Figure 18:
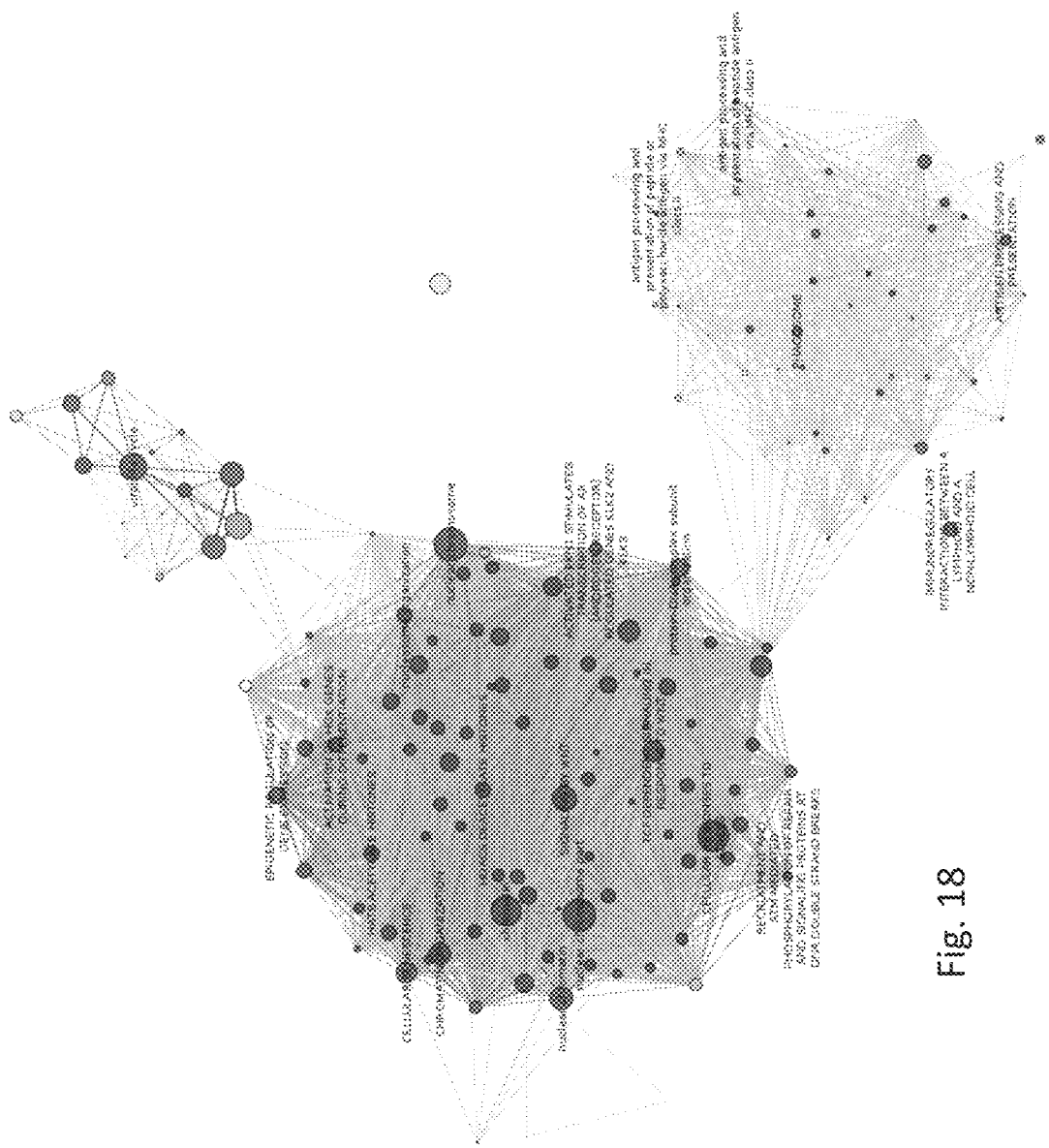
FIG. 18 shows pathway analysis for CNAs enriched in trunk or branch. Enrichment map showing pathways (Q<0.05, multiple testing correction using FDR) related to CNAs that were enriched in the trunk or branch from using Gene Ontology, KEGG, and Reactome. Enriched pathways from g:Profiler were filtered via a permutation analysis. The filtered pathways were visualized using Cytoscape (v3.4.0).
Figure 19:
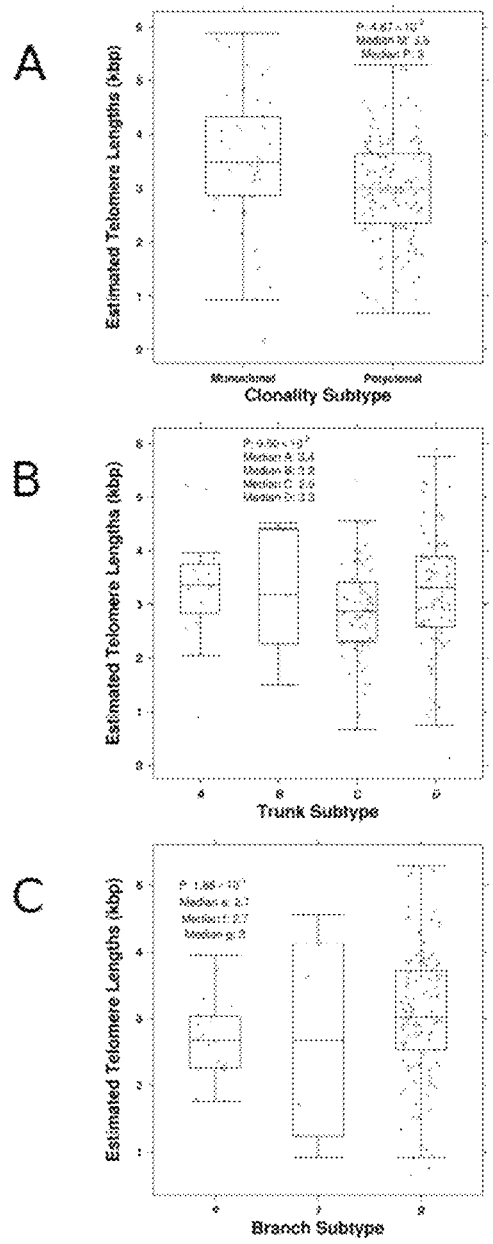
FIG. 19 shows subclonal associations of telomere length. (A) compares telomere lengths (estimated with TelSeq) between monoclonal and polyclonal tumours (Mann-Whitney U-test). (B) and (C) show telomere length of patients clustered into trunk and branch CNA subtypes, respectively, with the corresponding Kruskal-Wallis test P-value.
Figure 20:
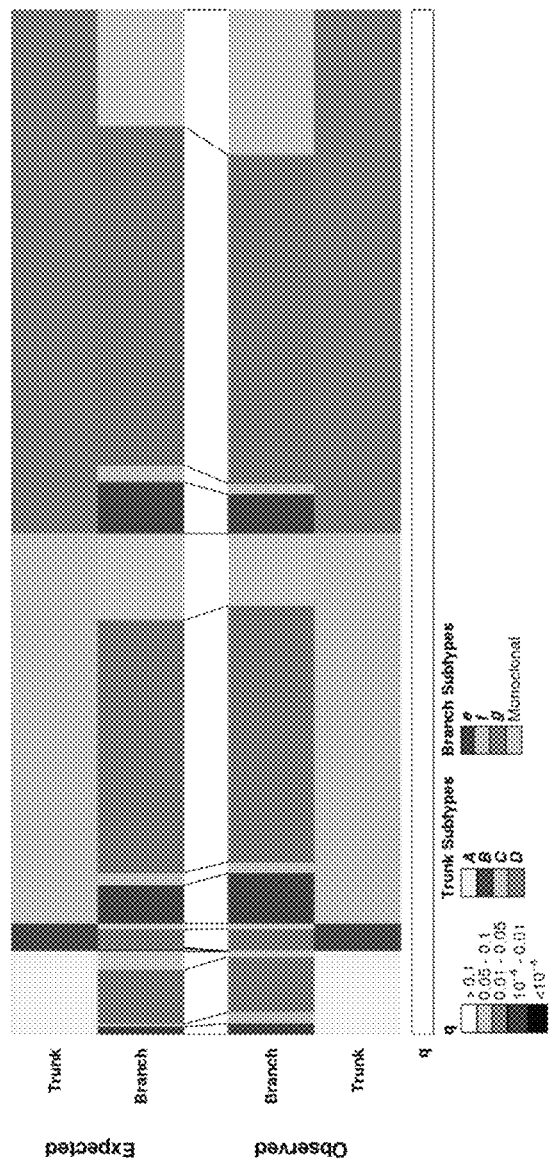
FIG. 20 shows trunk and branch subtype comparison. The concordance of trunk and branch subtypes is shown by comparing the expected proportion (at the top) to the observed proportion (middle) of patients in the pair subtypes along the x-axis. At the bottom is the Q-value addressing whether the proportion of patients classified in the pair of subtypes is different than expected by chance alone (Fisher's exact test).
Figure 21:
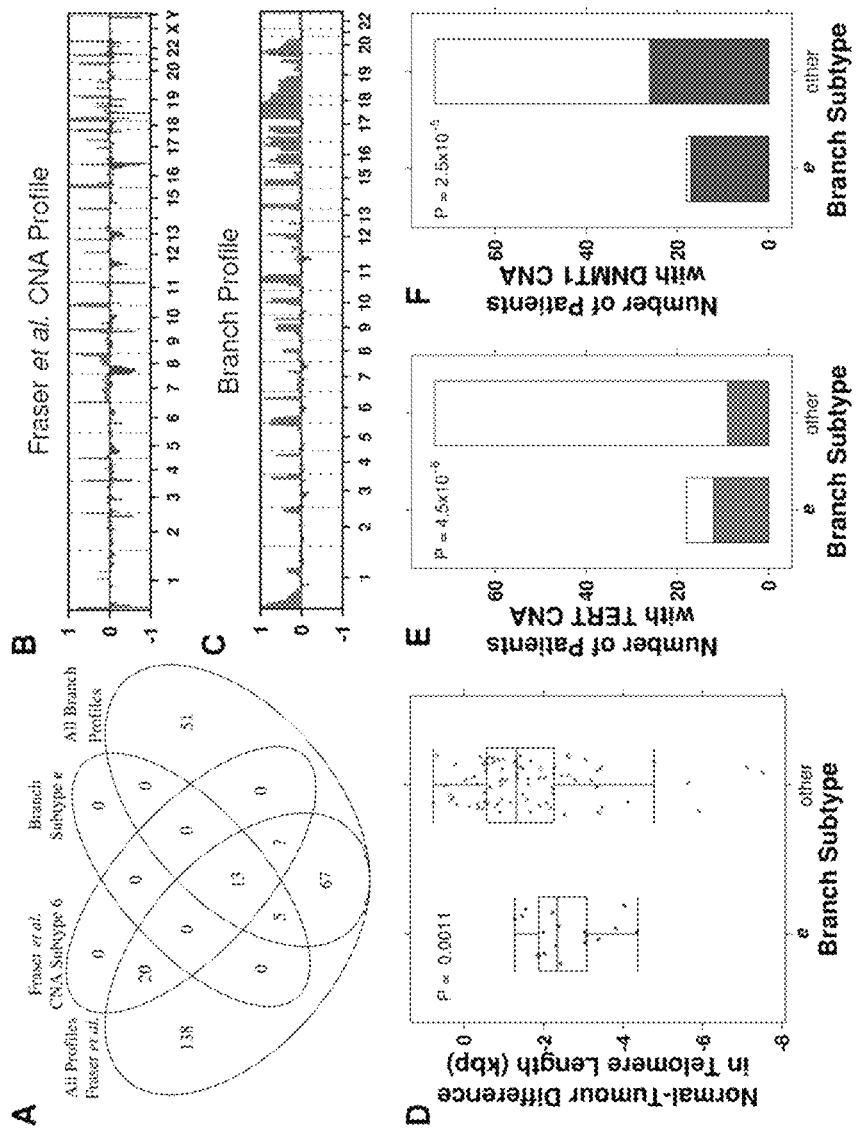
FIG. 21 shows subclonal association of telomere length with TERT and DNMT1. (A) Overlap between subtypes having subtelomeric gains. The average profile for the 18 patients in branch subtype e are shown in (B) using the CNA profiles from Fraser et al. and in (C) using the derived branch profiles. Gene gains are represented with red and gene losses are represented with blue. The difference between estimations of telomere length in the normal and tumour samples is shown in (ID) with the corresponding two-sided Wilcoxon test P-value comparing e patients to other patients. The number of patients with a gain of TERT in the overall Fraser et al. profiles is shown in (E) and the number of patients with loss of DNMT1 in the overall Fraser et al. profiles is shown in (F) with corresponding P-values testing for equal proportions between e patients and other patients (Pearson's $\chi^2$ test).
Figure 22:
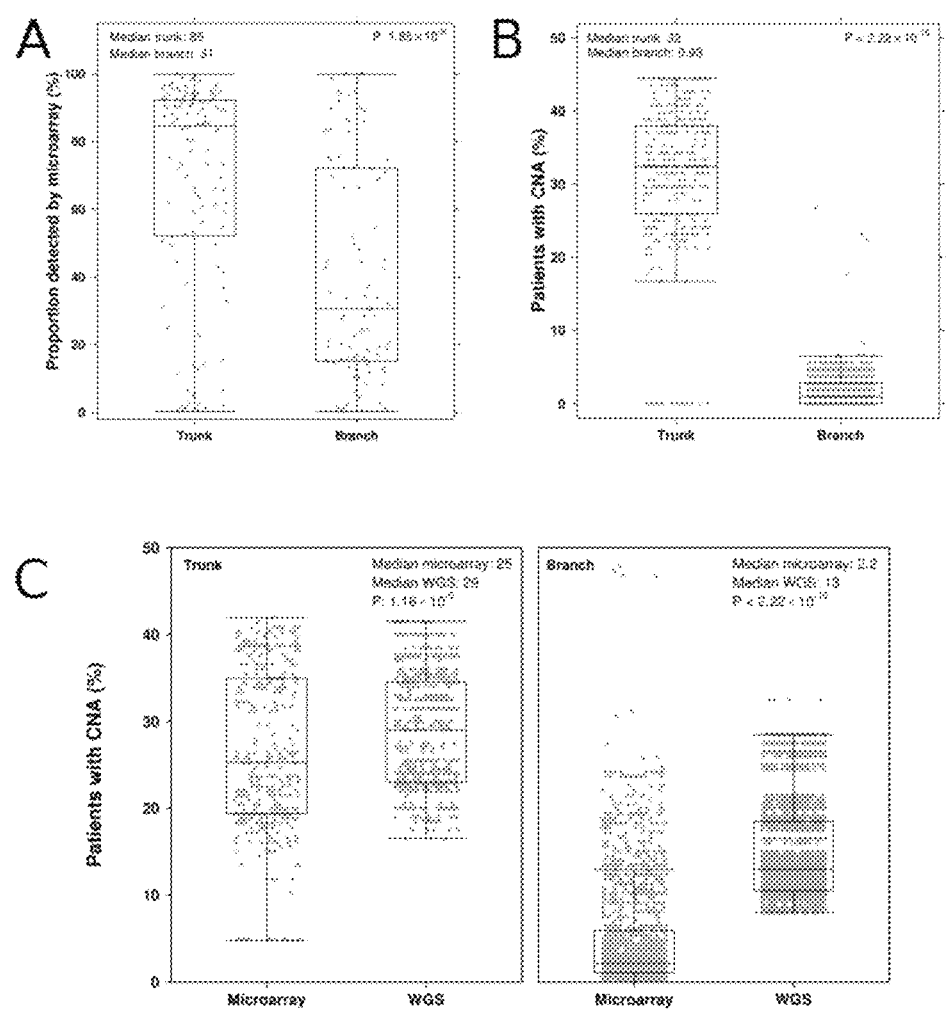
FIG. 22 shows microarray sensitivity. (A) Proportion of whole genome sequence-based CNAs in the trunk and branch that were also detected by microarrays. The recurrence of CNAs in the genes identified as differentially altered in trunk and branch are shown for microarray data from the Taylor dataset (B). This recurrence is contrasted between the two platforms, WGS and microarray, in this cohort (C). P-values from Mann-Whitney U-tests are shown in all three plots.
Figure 23:
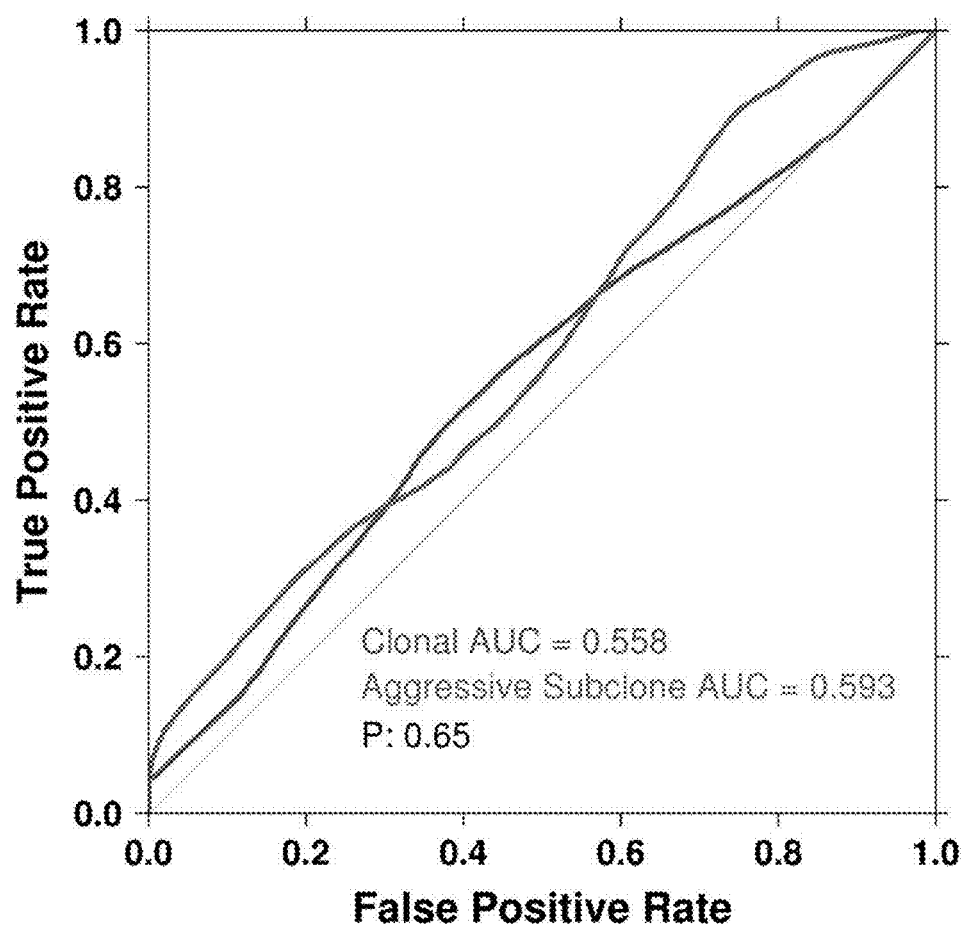
FIG. 23 shows PGA Biomarker AUC. Area under the receiver operator curve (AUC) for PGA with a cutoff of 7.49% applied to first cancer clone and subclone with the highest biomarker score.
Figure 24:
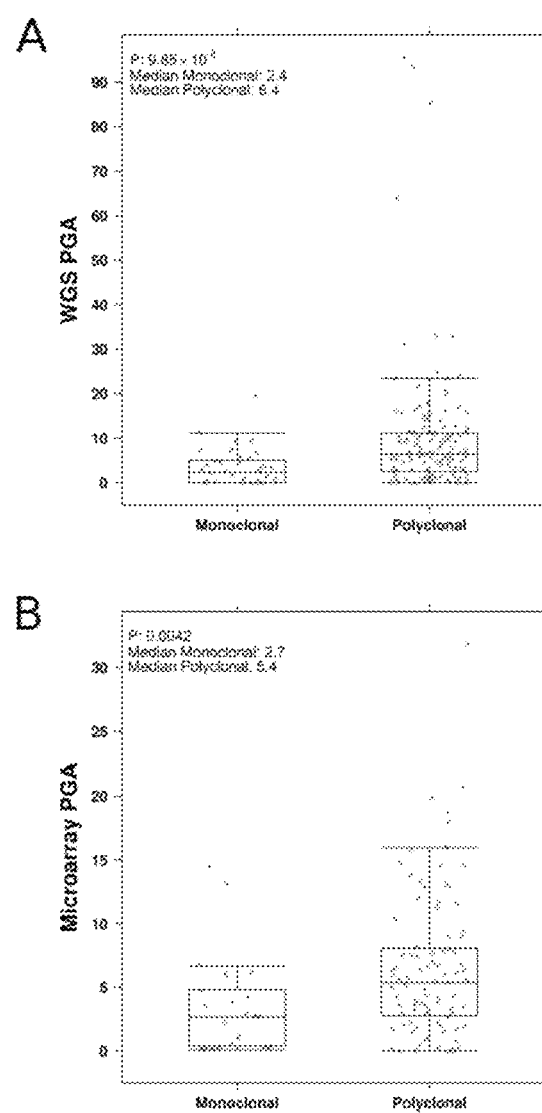
FIG. 24 shows PGA comparison and clonality. Monoclonal and polyclonal patients differ in their PGA irrespective of whether it is estimated by WGS (A) or microarray platforms (B).
Figure 25:
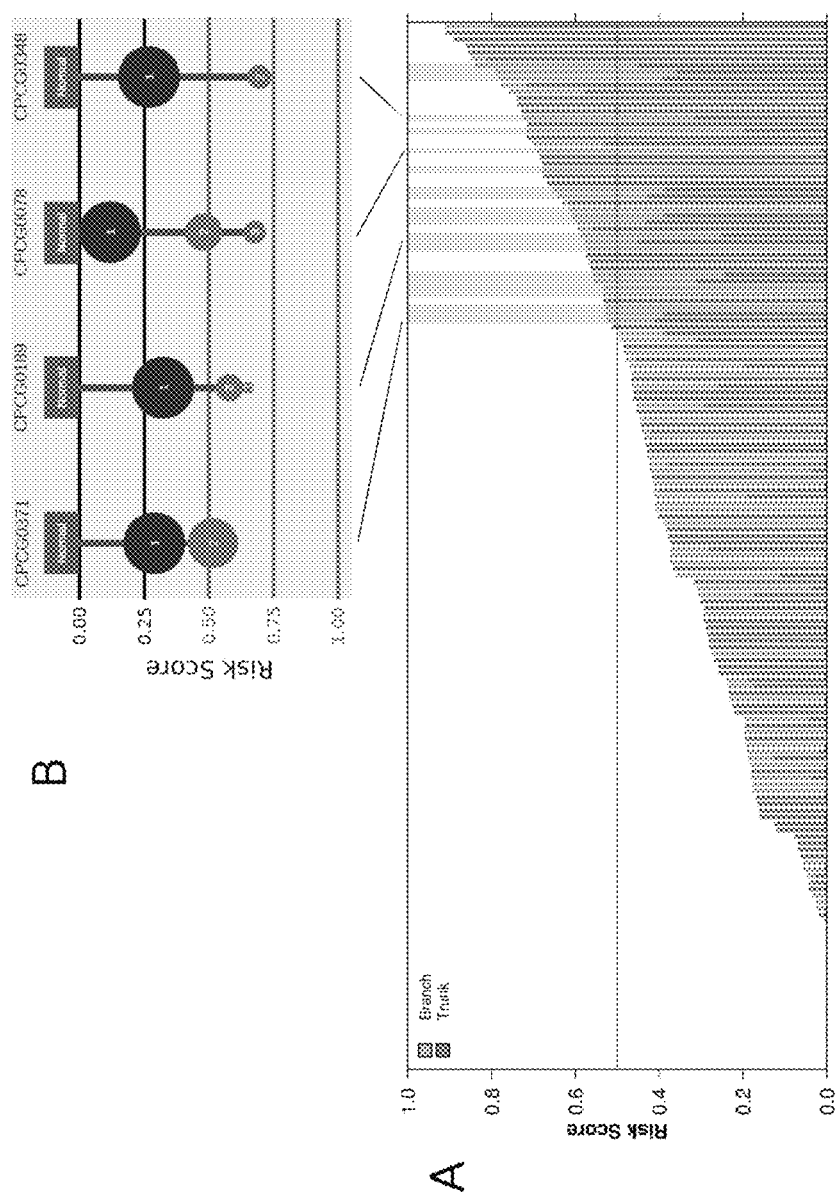
FIG. 25 shows risk score changes. (A) Risk score of 100-locus biomarker calculated for trunk mutations only, and all mutations in the tumour. The red line divides the low-risk (risk score<0.5) from the high-risk (risk score≥0.5) patients. Bars with a grey background indicate patients that are pushed to being high risk when considering CNAs that occur in their subclonal populations. Exemplars of these cases are shown in (B). Red outlines the turning point in which the patient becomes high risk.
Figure 26:
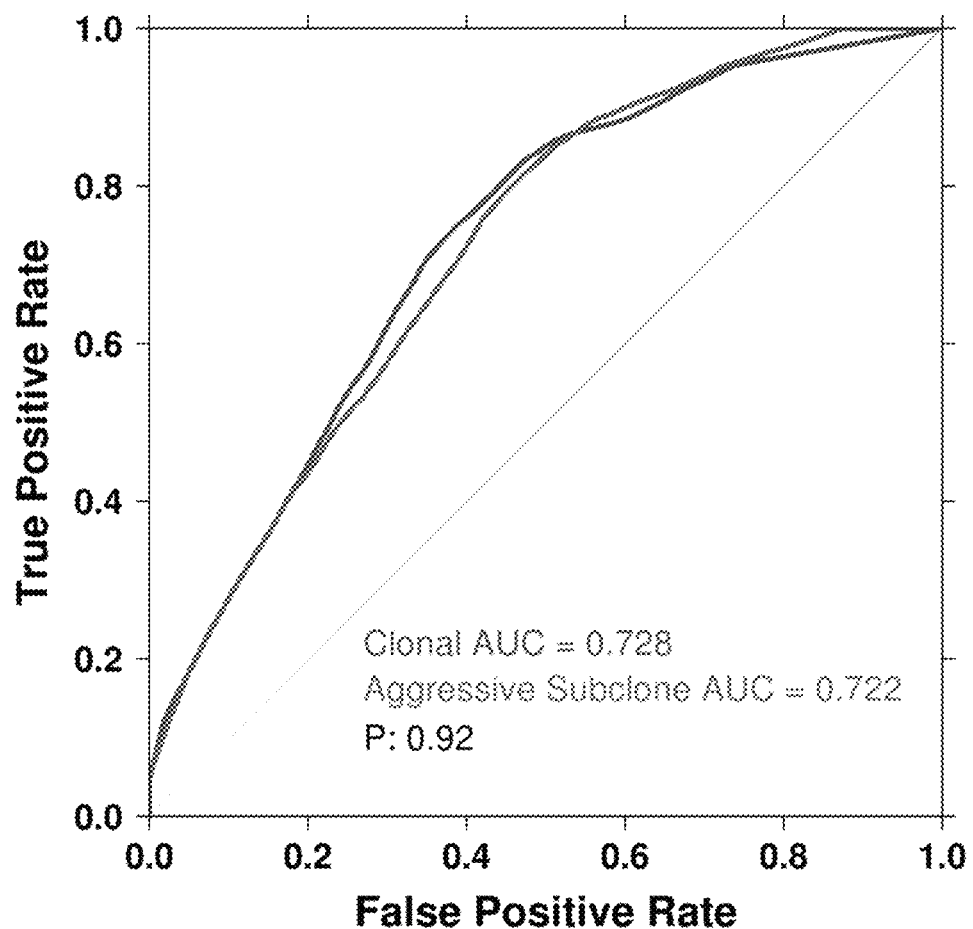
FIG. 26 shows risk score biomarker AUC. Area under the receiver operator curve (AUC) for the 100-locus risk score signature applied to the trunk and to the subclone with the highest risk score.
Figure 27:
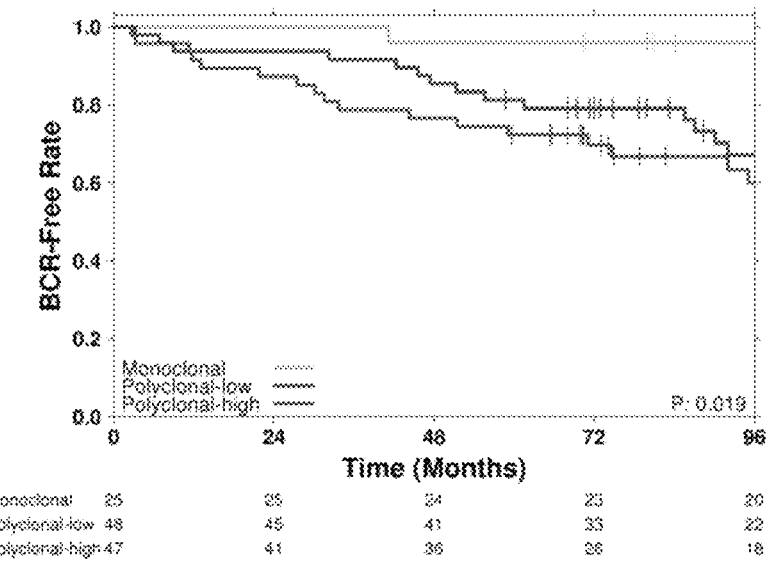
FIG. 27 shows PGA-Stratified survival curves. Survival outcomes of monoclonal and polyclonal samples, median dichotomized by PGA. Median dichotomization based on WGS-estimates of PGA is shown in (A) and microarray-based PGA estimates are used in (B).
Figure 27:
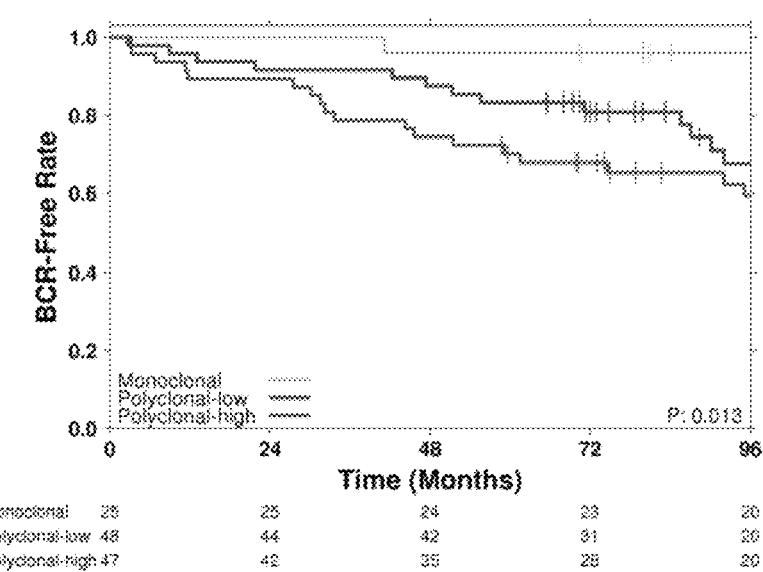

To determine if subclonal mutations are directly influencing the accuracy of existing biomarkers, we considered two validated DNA based prognostic tests: PGA (with an operating threshold of 7.49%) and a 100-locus genomic classifier[13]. We first assessed how accurately microarray-based CNA assays, which predominate the literature, detect subclonal CNAs (FIG. 17A). Arrays identified a large fraction of clonal CNAs detected by WGS (68.4±5.6%), but did not identify a large majority of subclonal CNAs (41.3±6.3%; $p=1.85\times10^{-8}$; Mann-Whitney U-test). We compared this finding with a different data set and came across similar insensitivity (FIG. 17B, and data not shown). This lack of sensitivity from microarray-based assays suggested that false-negatives in validated tests may result from rare aggressive subclones that were not detected (FIG. 17C). For PGA as a prognostic biomarker, we assessed for each patient what fraction of their risk derived from CNAs present in the trunk of the tumour and what fraction derived from subclonal CNAs only present in the most aggressive clone. On average, patients derived 58.3±6.18% of their risk from clonal CNAs and 41.7±6.18% from branch CNAs (FIG. 4B, FIG. 18, and data not shown). We identified 34/160 patients whose clonal risk-score predictions indicated low-risk disease, but who harboured aggressive high-risk subclones (FIG. 4C). Similar results were obtained using the 100-locus prognostic signature (FIGS. 19 and 20, and data not shown). Taken together, these data strongly suggest that incorporating information about tumour evolution into biomarker development will improve delivery of precision medicine.

Multi-region sequencing has demonstrated that single biopsy samples dramatically underestimate the mutation-content of individual tumours. Our analyses show that the molecular evolution of a tumour type can be viewed by analyzing large cohorts of such tumour samples. We identify a subset of driver mutations which occur later in prostate tumour development, and show that these aggregate into subtypes that reflect divergent and changing mutagenic stresses on tumours[20]. These molecular changes are directly associated with the aggressiveness of disease: patients with more subclones in their tumour show worse outcome, despite the underestimation of subclonality from ignoring spatio-genomic heterogeneity. Further, subclonal mutations are frequently missed by classic genomic profiling techniques like microarrays, and by considering them we change the predictions of molecular prognostic tests. These observations support the hypothesis that more genetically diverse tumours have inherently worse outcome, perhaps due an increased ability to adapt to therapeutic interventions. Combined with previous studies, a picture of the life-history of aggressive prostate cancer emerges. Tumours start with slow gradual accumulation of SNVs. In a subset of these, driver mutations or other phenomenon induce a switch to the rapid accumulation of copy number changes and evolutionary branching to create subclonal diversity. A subset of those subclones survive primary, definitive therapy and expand to form a host of related tumour clones that colonize, compete and collaborate across multiple metastatic sites[9]. This picture implies that early identification of tumours with high mutational burden and multiple subclones combined with aggressive genomes will improve cure rates through personalized therapy.

EXAMPLE 2

Figure 5:
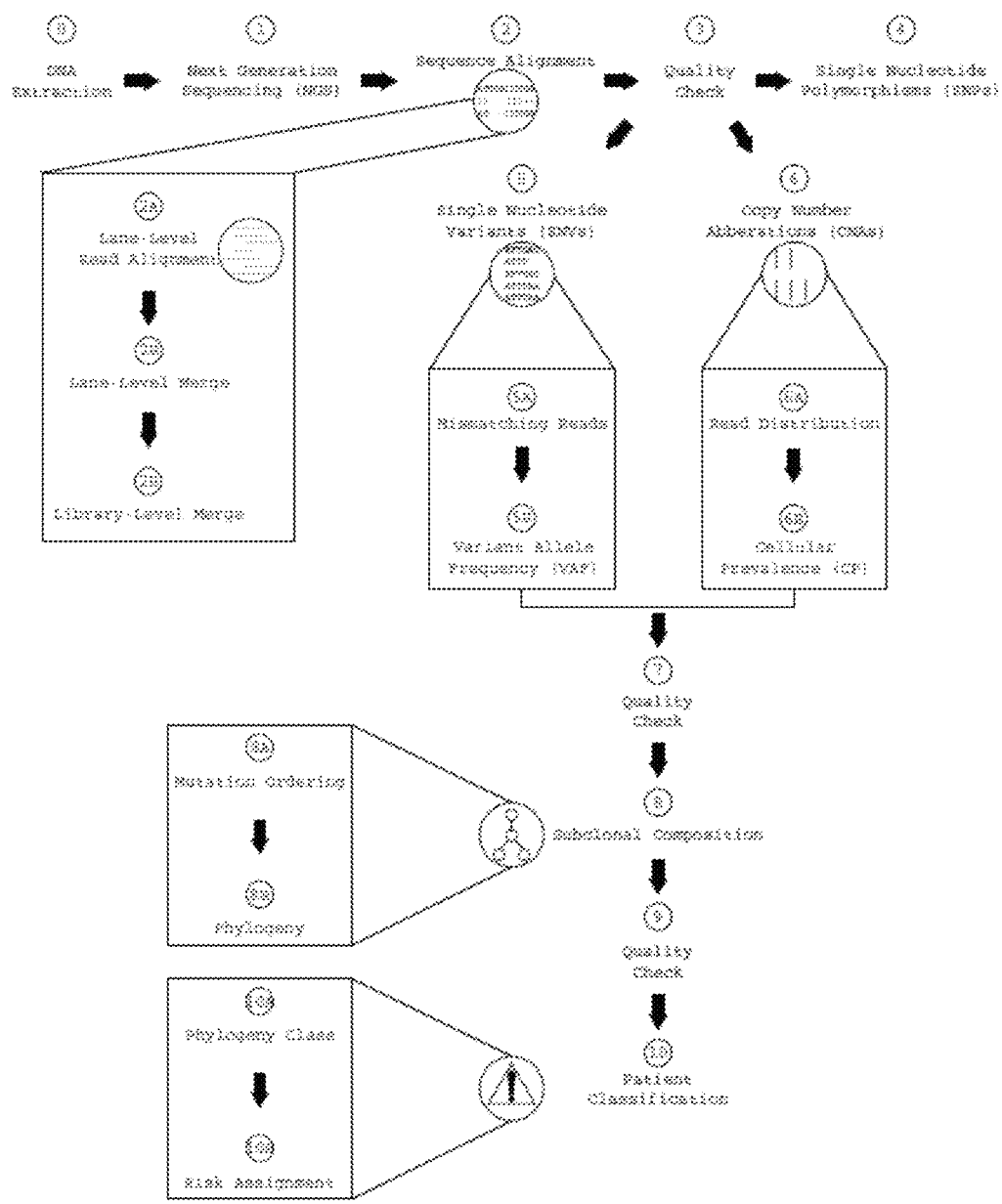
FIG. 5 shows a flow chart of an exemplary method for classifying cancer patients by risk, based on sequencing and clonality analysis.

We describe an exemplary method for diagnosing and/or prognosing a cancer in a subject based on the findings in Example 1. Reference is made to FIG. 5.

0. Raw Data

DNA samples are extracted from the patient with utmost care, trying to avoid any contamination from other sources. Ideally, normal and tumour tissue samples are both collected.

1. Next Generation Sequencing (NGS)

The raw data is sequenced using NGS (also known as high-throughout sequencing). This platform opens new ways and protocols in determining gene expression and identifying fundamental biological knowledge[1]. Sequencing can be performed at a whole-genome level, exome-level, de novo, or targeted at specific locations. A few modern sequencing technologies include Illumina Solexa sequencing[2], Roche 454 sequencing[3], Ion torrent and SOLiD sequencing[4]. These methods provide superior advantages over the previous Sanger sequencing technology[5] in terms of cost, speed, accuracy, and sample size.

2. Sequence Alignment

The raw sequencing data is aligned to some reference assembly. The goal is to reconstruct the genomic sequence of the patient. The normal and tumour data are aligned separately against a common reference, such as hg19, GRCh37, or GRCh38[6]. Some common alignment tools include the Burrows-Wheeler Aligner (BWA)[7], Novoalign[8], Bowtie[9], and SpeedSeq[10].

The next substeps can be applied to increase parallelization. 2A: A flowcell used during sequencing contains multiple lanes. Each lane consists of a set of paired-end reads, which can be aligned to the reference to generate an alignment file. 2B: All individual lane alignments that came from the same library preparation stage are merged together using tools like Picard[11]. 2C: Library alignments belonging to the same normal or tumour sample are merged together. Reads duplicated across different lanes are marked by tools like Picard to avoid double counting reads.

3. Alignment Quality Check

To ensure correct and best alignments, the resulting binary alignment/maps (BAMs) are ran through additional quality measurements. These include but are not limited to ensuring: expected read coverage of each BAM using tools like Genome Analysis Toolkit (GATK) DepthOfCoverage[12]; properly formatted BAM headers (contains unique sample name, list of read groups, etc.) using tools like SAMtools[13]; duplicative results by realignment using tools like GATK; and validity in downstream analysis by running downstream tools on a small subset of the BAMs. Checking validity may reveal sample preparation issues, sample swaps (switching normal for tumour sample, or normal of patient X with normal of patient Y), or contamination (occuring during the preparation stages of NGS).

4. Single Nucleotide Polymorphisms (SNPs)

The tumour sample can be compared with the normal sample to identify any sets of mutations. Germline mutations are those genetically inherited, compared to somatic mutations which are acquired throughout the patient's lifetime (see Step 5). Germline mutations are identified by comparing the normal sample to the reference (hg19, GRCh37, or GRCh38). A probability score is assigned to each mutation called and a score threshold applied to keep only confident calls. These mutations can be called by tools like GATK's UnifiedGenotyper or HaplotypeCaller, and VarScan 2[14]. An additional quality check for germline mutations can be applied by tools like ContEst[15] or Conpair[16] to check for any contamination at the sample level or lane level.

5. Single Nucleotide Variants (SNVs)

Somatic SNVs are identified from the NGS experiments by using models that compare the patient normal with their tumours. These SNVs can be driver mutations in the patient's cancer and play a significant role in tumour evolution. Tools that apply these models include but are not limited to SomaticSniper[17], MuTect[18], MutationSeq[19], Strelka[20], and Radia[21].

5A: These models detect anomalies in the tumour and normal alignments using the read information. They call variants that have a base mismatch in the tumour in majority of the reads when compared to the normal. Each variant call is assigned a probability or quality score to measure the accuracy of the call. A threshold is used to remove any probably false positives from the true positive variants. The base mismatch, position, and read depths are recorded for each variant.

5B: SNVs are the most common ways to determine subpopulations of cells, called subclones, within a tumour population. One indication of a subpopulation is through clusters of co-occurring mutations, which can be measured by looking at their variant allele frequencies (VAFs). VAF refers to the frequency of mutations in the tumour when compared to the normal, using the collection of SNVs in the sample—either the raw SNVs called by the models or after any quality checking. They can be calculated by counting the fraction of NGS reads supporting the mutation using tools like SAMtools, GATK, or alleleCount[22]. These clusters of mutations can be defined by using a distance metric (e.g. Euclidean), or assigning a probability of mutations belonging together.

6. Copy Number Aberrations (CNAs)

CNAs measure larger scale events and can affect up to an entire chromosome. They can be large scale duplications or deletions of chromosome regions. CNAs can be called using microarray assay technology, such as OncoScan Affymetrix[23], or by using whole-genome sequencing (WGS) methods like TITAN[24], Battenberg[25], and BIC-Seq[26]. Sample ploidy can be estimated from the total CNAs in the sample and regions of normal copy number can also be identified. Chromosomal regions with similar CNAs can indicate subclonal populations that arise from the tumour.

6A: CNAs are detected by changes in log R—a logarithmic ratio between tumour and normal read distribution in chromosomal regions. Log R also estimates the copy number for a given region and an overall ploidy can be estimated by averaging the total CNAs in the sample.

6B: Cellular prevalence (CP) defines the proportion of the tumour sample belonging to a subclone. They can be estimated from copy number differences between normal and tumour, and the VAF of the mutations across the subclones. Each CNA is annotated by CP, type of aberration (deletion/duplication, gain vs. loss), genomic location, and log R. Tools that provide these estimates include TITAN and Battenberg.

7. Callset Quality Check

Technology is not perfect—neither experimental nor computational methods. The set of variant calls (SNVs and CNAs) can be reduced to a set of confident calls. In a given cohort, the top X percent of recurring mutations may only be chosen. When running multiple tools and methods, a union or intersection of variant calls could be used. The calls can be further reduced by using known public data—a set of whitelist and blacklist mutations seen in another cohort—such as dbSNP[27] and the 1000 Genomes Project[28]. For CNAs which may vary largely in length, a minimum or maximum CNA length could be applied.

8. Subclonal Composition

Once potential subclones are identified, the goal is to link them together and reconstruct their phylogenetic relationships—does subclone B arise from subclone A, or are they two distinct subclones? Do they share a common ancestor, and if so, what mutations differentiate them? In what order do these mutations occur?

8A: Computational approaches that can assess this problem include PhyloWGS[29], PhyloSub[30], PyClone[31], SciClone[32], and ThetA[33]. They measure the likelihood that SNVs and CNAs co-occur and cluster them based on cal and CP. Each cluster would have a set of mutations assigned to it.

8B: Using the predicted clusters, subpopulations can be ordered by standardizing some rules. For one, a subclone with lower CP must occur later in evolution than subclone with higher CP. In addition, subclones arising from the same parent population must have their CP sum bounded by the CP of the parent population. Multiple phylogenies can be generated and the most probably phylogeny is used.

9. Subclonality Quality Check

To ensure accurate phylogenetic reconstructions, the subclonal compositions can be compared across different tools and multiple runs. Runs can consist of a subset of the mutation callset rather than all mutations, and may consider fewer or more iterations of the methodology. To reduce false positive subclones, thresholds can be applied, such as minimum CP, minimum number of mutations, minimum percent genome alteration, or maximum number of subclones. Subclones that do not pass thresholds may be removed or merged together to represent a subclone at a higher phylogeny.

10. Patient Classification

Patients are classified into risk levels, as assessed by the subclonal evolution of their tumours.

10A: Final phylogenetic trees can be classified in different ways, such as by shape (linear vs. branching), number of subpopulations (e.g. monoclonal for a single population, polyclonal for >1), or number of ancestral tumours (e.g. polytumours).

10B: Patient risk can be classified by characteristics that pertain to their survival, such as biochemical recurrence (BCR) and time to BCR. Patients are grouped according to their phylogeny (e.g. monoclonal vs. polyclonal vs. polytumour) defined by their subclonal composition. Survival models such as the Cox Proportional-Hazards Regression (coxPH)[34] are fit to the cohort and survival Kaplan-Meier curves plotted to predict patient risk.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST EXAMPLE 1

1 Stephens, P. J. et al. Massive genomic rearrangement acquired in a single catastrophic event during cancer development. *Cell* 144, 27-40, doi:10.1016/j.cell.2010.11.055 (2011).

2 Vogelstein, B. et al. Genetic alterations during colorectal-tumor development. *The New England journal of medicine* 319, 525-532, doi:10.1056/NEJM198809013190901 (1988).

3 Gerlinger, M. et al. Intratumor heterogeneity and branched evolution revealed by multiregion sequencing. *N Engl J Med* 366, 883-892, doi:10.1056/NEJMoa1113205 (2012).

4 McPherson, A. et al. Divergent modes of clonal spread and intraperitoneal mixing in high-grade serous ovarian cancer. *Nature genetics* 48, 758-767, doi:10.1038/ng.3573 (2016).

5 Nik-Zainal, S. et al. The life history of 21 breast cancers. *Cell* 149, 994-1007, doi:10.1016/j.cell.2012.04.023 (2012).

6 Boutros, P. C. et al. Spatial genomic heterogeneity within localized, multifocal prostate cancer. *Nature Genetics* 47, 736-745, doi:10.1038/ng.3315 (2015).

7 Cooper, C. S. et al. Analysis of the genetic phylogeny of multifocal prostate cancer identifies multiple independent clonal expansions in neoplastic and morphologically normal prostate tissue. *Nat. Genet.* 47, 367-372, doi:10.1038/ng.3221 (2015).

8 The Cancer Genome Atlas Network. The Molecular Taxonomy of Primary Prostate Cancer. *Cell* 163, 1011-1025, doi:10.1016/j.cell.2015.10.025 (2015).

9 Gundem, G. et al. The evolutionary history of lethal metastatic prostate cancer. *Nature* 520, 353-357, doi:10.1038/nature14347 (2015).

10 Pritchard, C. C. et al. Inherited DNA-Repair Gene Mutations in Men with Metastatic Prostate Cancer. *The New England journal of medicine* 375, 443-453, doi:10.1056/NEJMoa1603144 (2016).

11 Demichelis, F. et al. Distinct genomic aberrations associated with ERG rearranged prostate cancer. *Genes, chromosomes & cancer* 48, 366-380, doi:10.1002/gcc.20647 (2009).

12 Hong, M. K. et al. Tracking the origins and drivers of subclonal metastatic expansion in prostate cancer. *Nature communications* 6, 6605, doi:10.1038/ncomms7605 (2015).

13 Lalonde, E. et al. Tumour genomic and microenvironmental heterogeneity for integrated prediction of 5-year biochemical recurrence of prostate cancer: a retrospective cohort study. *Lancet Oncol* 15, 1521-1532, doi:10.1016/S1470-2045(14)71021-6 (2014).

14 Cuzick, J. et al. Prognostic value of an RNA expression signature derived from cell cycle proliferation genes in patients with prostate cancer: a retrospective study. *The Lancet. Oncology* 12, 245-255, doi:10.1016/S1470-2045(10)70295-3 (2011).

15 Erho, N. et al. Discovery and validation of a prostate cancer genomic classifier that predicts early metastasis following radical prostatectomy. *PLoS One* 8, e66855, doi:10.1371/journal.pone.0066855 (2013).

16 Klein, E. A. et al. A 17-gene assay to predict prostate cancer aggressiveness in the context of Gleason grade heterogeneity, tumor multifocality, and biopsy undersampling. *Eur Urol* 66, 550-560, doi:10.1016/j.eururo.2014.05.004 (2014).

17 Hieronymus, H. et al. Copy number alteration burden predicts prostate cancer relapse. *Proceedings of the National Academy of Sciences of the United States of America* 111, 11139-11144, doi:10.1073/pnas.1411446111 (2014).

18 Taylor, B. S. et al. Integrative genomic profiling of human prostate cancer. *Cancer Cell* 18, 11-22, doi:10.1016/j.ccr.2010.05.026 (2010).

19 Ross-Adams, H. et al. Integration of copy number and transcriptomics provides risk stratification in prostate cancer: A discovery and validation cohort study. *EBioMedicine* 2, 1133-1144, doi:10.1016/j.ebiom.2015.07.017 (2015).
20 de Bruin, E. C, et al. Spatial and temporal diversity in genomic instability processes defines lung cancer evolution. *Science* 346, 251-256, doi:10.1126/science.1253462 (2014).
21 Ha, G. et al. TITAN: inference of copy number architectures in clonal cell populations from tumor whole-genome sequence data. *Genome Res.* 24, 1881-1893, doi:10.1101/gr.180281.114 (2014).
22 Deshwar, A. G. et al. PhyloWGS: Reconstructing subclonal composition and evolution from whole-genome sequencing of tumors. *Genome Biol.* 16, 35, doi:10.1186/s13059-015-0602-8 (2015).
23 Wang, K., Li, M. & Hakonarson, H. ANNOVAR: functional annotation of genetic variants from high-throughput sequencing data. *Nucleic Acids Res.* 38, e164, doi:10.1093/nar/gkq603 (2010).
24 Wilkerson, M. D. & Hayes, D. N. ConsensusClusterPlus: a class discovery tool with confidence assessments and item tracking. *Bioinformatics* 26, 1572-1573, doi:10.1093/bioinformatics/btq170 (2010).
25 Senbabaoglu, Y., Michailidis, G. & Li, J. Z. Critical limitations of consensus clustering in class discovery. *Sci Rep* 4, 6207, doi:10.1038/srep06207 (2014).
26 Reimand, J. et al. g:Profiler-a web server for functional interpretation of gene lists (2016 update), *Nucleic acids research, doi:*10.1093/nar/gkw199 (2016).
27 Pinto, D. et al. Functional impact of global rare copy number variation in autism spectrum disorders. *Nature* 466, 368-372, doi:10.1038/nature09146 (2010).
28 Alexandrov, L. B. et al. Signatures of mutational processes in human cancer. *Nature* 500, 415-421, doi:10.1038/nature12477 (2013).

REFERENCE LIST EXAMPLE 2

1. Mardis E. R. Next-generation DNA sequencing methods. Annual Review of Genomics and Human Genetics. 2008; 9:387-402. doi: 10.1146/annurev.genom.9.081307.164359.
2. Illumina. A high-resolution view of the entire genome. illumina.com.
3. Soares A. R. et al. Next-generation sequencing of miRNAs with Roche 454 GS-FLX technology: steps for a successful application. Methods in Molecular Biology. 2012; 822:189-204. doi: 10.1007/978-1-61779-427-8_13.
4. ThermoFisher Scientific. Ion Torrent next-generation sequencing technology. thermofisher.com.
5. Sanger F. et al. DNA sequencing with chain-terminating inhibitors. Proceedings of the National Academy of Sciences. U.S.A. 1977; 74:5463-5467. 10.1073/pnas.74.12.5463.
6. Genome Reference Consortium. ncbi.nlm.nih.gov.
7. Li H. et al. Fast and accurate short read alignment with Burrows-Wheeler transform. Bioinformatics. 2009; 25(14):1754-1760. doi: 10.1093/bioinformatics/btp324.
8. Novocraft. 2010. novocraft.com.
9. Langmead B. et al. Ultrafast and memory-efficient alignment of short DNA sequences to the human genome. Genome Biology. 2008; 10:R25-5. doi: 10.1186/gb-2009-10-3-r25.
10. Chiang C. et al. SpeedSeq: ultra-fast personal genome analysis and interpretation. Nature Methods. 2015; 12:966-968. doi: 10.1038/nmeth.3505.
11. Picard. broadinstitute.github.io.
12. McKenna A. et al. The Genome Analysis Toolkit: a MapReduce framework for analyzing next-generation DNA sequencing data. Genome Research. 2010; 20:1297-1303. doi: 10.1101/gr.107524.110.
13. Li H. et al. The sequence alignment/map format and SAMtools. Bioinformatics. 2009; 25:2078-2079.
14. Koboldt D. C. et al. Using VarScan 2 for germline variant calling and somatic mutation detection. Current Protocols in Bioinformatics. 2013; 44:15.4.1-15.4.17. doi: 10.1002/0471250953.bi1504s44.
15. Cibulskis K. et al. ContEst: estimating cross-contamination of human samples in next-generation sequencing data. Bioinformatics. 2011; 27(18):2601-2602. doi: 10.1093/bioinformatics/btr446.
16. Bergmann E. A. et al. Conpair: concordance and contamination estimator for matched tumor-normal pairs. Bioinformatics. 2016; 32(20):3196-3198. doi: 10.1093/bioinformatics/btw389.
17. Larson D. E. et al. SomaticSniper: identification of somatic point mutations in whole genome sequencing data. Bioinformatics. 2012; 28:311-317. doi: 10.1093/bioinformatics/btr665.
18. Cibulskis K. et al. Sensitive detection of somatic point mutations in impure and heterogeneous cancer samples. Nature Biotechnology. 2013; 31(3):213-219. doi: 10.1038/nbt.2514.
19. Ding J. et al. Feature-based classifiers for somatic mutation detection in tumour-normal paired sequencing data. Bioinformatics. 2012; 28:167-175. doi: 10.1093/bioinformatics/btr629.
20. Saunders C. T. et al. Strelka: accurate somatic small-variant calling from sequenced tumor-normal sample pairs. Bioinformatics. 2012; 28(14):1811-7. doi: 10.1093/bioinformatics/bts271.
21. Radenbaugh A. J. et al. Radia: RNA and DNA integrated analysis for somatic mutation detection. PLoS One. 2014; 9:e111516. doi:10.1371/journal.pone.0111516.
22. Cancerit. AlleleCount. github.com.
23. Dalma-Weiszhausz D. D. et al. The affymetrix GeneChip® platform: An overview. Methods in Enzymology. 2006; 410:3-28. doi 10.1016/S0076-6879(06)10001-4.
24. Ha G. et al. TITAN: inference of copy number architectures in clonal cell populations from tumor whole-genome sequence data. Genome Research. 2014; 24(11):1881-1893. doi: 10.1101/gr.180281.114.
25. Cancerit. Battenberg. github.com.
26. Xi R. et al. BIC-seq: a fast algorithm for detection of copy number alterations based on high-throughput sequencing data. Genome Biology. 2010; 11(S1):O10. doi: 10.1186/gb-2010-11-s1-o10.
27. Bhagwat M. Searching NCBI's dbSNP database. Current Protocols in Bioinformatics. 2010; 1:1-19. doi: 10.1002/0471250953.bi0119s32.
28. The 1000 Genomes Project Consortium. A global reference for human genetic variation. Nature. 2015; 526:68-74. doi: 10.1038/nature15393.
29. Deshwar A. G. et al. PhyloWGS: reconstructing subclonal composition and evolution from whole-genome sequencing of tumors. Genome Biology. 2015; 16:35. doi: 10.1186/s13059-015-0602-8.
30. Jiao W. et al. Inferring clonal evolution of tumors from single nucleotide somatic mutations. BMC Bioinformatics. 2014; 15:35. doi: 10.1186/1471-2105-15-35.
31. Roth A. et al. PyClone: statistical inference of clonal population structure in cancer. Nature Methods. 2014; 11(4):396-398. doi: 10.1038/nmeth.2883.

32. Miller C. A. et al. SciClone: inferring clonal architecture and tracking the spatial and temporal patterns of tumor evolution. PLoS Computational Biology. 2014; 10:e1003665 doi: 10.1371/journal.pcbi.1003665.
33. Oesper L. et al. THetA: inferring intra-tumor heterogeneity from high-throughput DNA sequencing data. Genome Biology. 2013; 14:R80. doi: 10.1186/gb-2013-14-7-r80.
34. George B. et al. Survival analysis and regression models. Journal of Nuclear Cardiology. 2014; 21(4):686-694. doi: 10.1007/s12350-014-9908-2.

The invention claimed is:

1. A method of treating cancer in a subject comprising the step of administering a therapeutic intervention to the subject, wherein the subject has been determined to have cancer sensitive to the therapeutic intervention from a method that provides whole-genome cancer DNA sequencing data from a cancer sample comprising cancer DNA from the subject; compares the whole-genome cancer DNA sequencing data with control DNA sequencing data to determine genetic aberrations; determines, from the genetic aberrations, the clonal and subclonal populations present in the sample; and constructs a phylogenetic map of the clonal and subclonal populations, wherein the clonal and subclonal populations and phylogenetic map determine whether the subject has cancer sensitive to the therapeutic intervention, wherein the therapeutic intervention comprises surgery when the cancer is determined to be monoclonal with 95% confidence, and wherein the therapeutic intervention comprises radiotherapy when the cancer is determined to be polyclonal with 95% confidence.

2. The method of claim 1, wherein the control DNA sequencing data is DNA sequencing data from a sample comprising normal cells from the subject.

3. The method of claim 1, wherein the cancer sample comprises cancer cells.

4. The method of claim 1, wherein the whole-genome sequencing cancer DNA sequencing data is generated using high-throughput sequencing.

5. The method of claim 1, wherein the method used to determine the subject to have cancer sensitive to the therapeutic intervention further comprises a sequence alignment of the DNA sequencing data against a common reference assembly to generate binary alignment/maps (BAMs) or sequence alignment maps (SAMs).

6. The method of claim 1, wherein the method used to determine the subject to have cancer sensitive to the therapeutic intervention further performs a sequence alignment quality check.

7. The method of claim 6, wherein the sequence alignment quality check comprises at least one of: ensures expected read coverage of each BAM; ensuring properly formatted BAM headers; removes duplicative reads by soft-or hard-filtering, improving alignment quality by local realignment; and performs validity downstream analysis on a small subset of the BAMs.

8. The method of claim 1, wherein the genetic aberrations comprise at least one of single nucleotide variants and copy number aberrations.

9. The method of claim 1, wherein the method used to determine the subject to have cancer sensitive to the therapeutic intervention further performs a callset quality check.

10. The method of claim 9, wherein the callset quality check comprises at least one of: applies a recurrence, intersection or union of calls; filters out non-confidence calls against known whitelists and blacklists; and maintains specific length of copy number aberrations.

11. The method of claim 1, wherein the determines step is performed by a step comprising determining at least one of the variant allele frequencies and cellular prevalence.

12. The method of claim 1, wherein the constructs step is performed by a step comprising clustering the subclonal populations based on variant allele frequencies and cellular prevalence.

13. The method of claim 1, wherein the cancer is prostate cancer.

* * * * *